United States Patent
Tang et al.

(10) Patent No.: US 11,629,289 B2
(45) Date of Patent: Apr. 18, 2023

(54) DONOR-ACCEPTOR AGGREGATION-INDUCED EMISSION LUMINOGEN WITH MULTI-STIMULI RESPONSIVE BEHAVIOR

(71) Applicant: The Hong Kong University of Science and Technology, Hong Kong (CN)

(72) Inventors: Benzhong Tang, Hong Kong (CN); Jing Zhang, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 359 days.

(21) Appl. No.: 15/929,344

(22) Filed: Apr. 28, 2020

(65) Prior Publication Data
US 2020/0354628 A1 Nov. 12, 2020

Related U.S. Application Data

(60) Provisional application No. 62/920,554, filed on May 6, 2019.

(51) Int. Cl.
*C09K 11/06* (2006.01)
*C07F 5/02* (2006.01)
(Continued)

(52) U.S. Cl.
CPC .......... *C09K 11/06* (2013.01); *C07C 211/56* (2013.01); *C07F 5/027* (2013.01); *G01N 21/64* (2013.01); *H01L 51/008* (2013.01); *H01L 51/0059* (2013.01); *C09K 2211/1007* (2013.01); *H01L 51/0031* (2013.01); *H01L 51/5012* (2013.01)

(58) Field of Classification Search
CPC .......... C09K 11/06; C09K 2211/1007; C09K 2211/1014; C07C 211/56; C07F 5/027; G01N 21/64; G01N 21/6428; G01N 21/643; G01N 2021/6432; H01L 51/0059; H01L 51/008; H01L 51/0031; H01L 51/5012; H01L 51/5004; H01L 2251/552; H01L 51/50
See application file for complete search history.

(56) References Cited

U.S. PATENT DOCUMENTS 7,507,485 B2 * 3/2009 Oh ........................ C09B 15/00
313/506
7,597,967 B2 * 10/2009 Kondakova ............ C09K 11/06
313/506
(Continued)

FOREIGN PATENT DOCUMENTS

| CN | 103483327 A | 1/2014 |
| CN | 103484104 A | 1/2014 |
| CN | 107652189 A * | 2/2018 |

OTHER PUBLICATIONS

Turkoglu G, Cinar ME, Ozturk T. Triarylborane-Based Materials for OLED Applications. Molecules. 2017; 22(9):1522. (Year: 2017).*
Pron, A., Baumgarten, M., & Müllen, K. (2010). Phenylene bridged boron—Nitrogen containing dendrimers. Organic Letters, 12(19), 4236-4239. (Year: 2010).*

(Continued)

*Primary Examiner* — Dawn L Garrett
(74) *Attorney, Agent, or Firm* — S&F/WEHRW

(57) ABSTRACT

Provided herein are aggregation-induced emission luminogens, methods of preparation and use thereof, and devices and sensors comprising the same. The aggregation-induced emission luminogens can exhibit multi-stimuli responsive emissions.

8 Claims, 36 Drawing Sheets

(51) Int. Cl.
*H10K 85/60* (2023.01)
*G01N 21/64* (2006.01)
*C07C 211/56* (2006.01)
*H10K 85/30* (2023.01)
*H10K 50/11* (2023.01)
*H10K 71/70* (2023.01)
*H01L 51/00* (2006.01)
*H01L 51/50* (2006.01)

(56) References Cited

U.S. PATENT DOCUMENTS

2003/0152800 A1* 8/2003 Tamao ................. C07F 5/027
                                                  252/301.16
2015/0236274 A1* 8/2015 Hatakeyama .......... C07F 5/02
                                                  548/405

OTHER PUBLICATIONS

Machine translation of CN 107652189 A (publication date Feb. 2018). (Year: 2018).*

Mater. Horiz., 2020, 7, pp. 135-142. (Year: 2020).*

Xu et al.; A new ligand and its complex with multi-stimuli-responsive and aggregation-induced emission effects; Chemical Communications; 2011; vol. 47; p. 11080-11082.

Dou et al.; Multi-stimuli-responsive fluorescence switching of a donor- acceptor π-conjugated compound; The Journal of Physical Chemistry Letters; 2011; vol. 2; pp. 666-670.

Zhu et al.; An AIE-active boron-difluoride complex: multi-stimuli-responsive fluorescence and application in data security protection; Chemical Communications; 2014; vol. 50; pp. 12951-12954.

Reus et al.; Stimuli-responsive chromism in organophosphorus chemistry; Dalton Trans.; 2016; vol. 45; pp. 1850-1855.

* cited by examiner

- Aggregation-Induced Emission
- Solvatochromic Photoluminescence (PL)
- Thermochromic PL
- Mechanochromic PL
- Electrochromism
- Electroluminochromism
- Electroluminescence Table 1. Photophysical properties of compound 1 in different solvents.

| Solvent | $v_a^{a)}$ (nm) | $v_f^{a)}$ (nm) | $v_a$-$v_f^{b)}$ (cm$^{-1}$) | $f^{c)}$ | $\Phi^{d)}$ (%) |
|---|---|---|---|---|---|
| Hexane | 390 | 476 | 4567 | 0.0012 | 41.3 |
| Triethylamine | 390 | 498 | 5561 | 0.048 | 40.9 |
| Isopropyl ether | 390 | 533 | 6879 | 0.145 | 31.2 |
| Ethyl ether | 390 | 542 | 7191 | 0.167 | 31.7 |
| Ethyl acetate | 390 | 559 | 7752 | 0.2 | 6.7 |
| THF | 390 | 562 | 7847 | 0.21 | 8.3 |
| DCM | 390 | 575 | 8250 | 0.217 | 3.7 |
| DMF | 390 | 590 | 8692 | 0.276 | 0.8 |
| Acetone | 390 | 597 | 8891 | 0.284 | 1.1 |
| Acetonitrile | 390 | 608 | 9194 | 0.305 | 0.5 |

Table 2. Crystal data and parameters of data collection and refinement for compound 1.[a)]

| Compound | 1 |
|---|---|
| Empirical formula | $C_{46}H_{45}BN_2$ |
| Formula weight | 660.67 |
| Temperature | 100(2) K |
| Wavelength | 1.54184 Å |
| Crystal system | Monoclinic |
| Space group | $P12_1/c1$ |
| Unit cell dimensions | $a$ = 7.5979(2) (12) Å |
| | $b$ = 32.4387(6) Å |
| | $c$ = 16.8075(4) Å |
| | $α$ = 90° |
| | $β$ = 115.761(2)° |
| | $γ$ = 90° |
| Volume | 3730.77(16) Å$^3$ |
| Z | 4 |
| Density (calculated) | 1.176 Mg/m$^3$ |
| Absorption coefficient | 0.507 mm$^{-1}$ |
| $F(000)$ | 1408 |
| Crystal size | 0.20 × 0.20 × 0.20 mm$^3$ |
| Theta range for data collection | 3.687 to 67.498° |
| Index ranges | -9≤$h$≤9, -26≤$k$≤40, -19≤$l$≤20 |
| Reflections collected | 21716 |
| Independent reflections | 7393 [$R$(int) = 0.0305] |
| Completeness to theta = 66.500° | 99.5 % |
| Refinement method | Full-matrix least-squares on $F^2$ |
| Data / restraints / parameters | 7393 / 0 / 464 |
| Goodness-of-fit on $F^2$ | 1.068 |
| Final R indices [$I$>2sigma($I$)] | $R1$ = 0.0592, $wR2$ = 0.1532 |
| R indices (all data) | $R1$ = 0.0755, $wR2$ = 0.1638 |
| Extinction coefficient | n/a |
| Largest diff. peak and hole | 0.297 and -0.235 e.Å$^{-3}$ |

FIG. 18

Table 3. Experimental and DFT calculation simulated (B3LYP/6-31G(d)) Raman internal modes of compound 1.

| Experimental value (cm$^{-1}$) | Theoretical value (cm$^{-1}$) | Vibrational mode |
|---|---|---|
| 709 | 737 | C–H bond off-plane wagging vibration |
| 723 | 741 | C–H bond off-plane wagging vibration |
| 740 | 757 | C–H bond off-plane wagging vibration |
| 997 | 1016 | breathing vibration of benzene ring (P1, P2 and P4) |
| 1002 | 1034 | breathing vibration of benzene ring (P3 and P5) |

Table 4. Photophysical properties of compound 1 at solid state.

| | HOMO/LUMO[a] (eV) | $T_d$[b] (°C) | $\lambda_{em}$[c] (nm) | $\Phi_F$[c] (%) | $\tau$[c] (ns) |
|---|---|---|---|---|---|
| 1 | -5.18 / -2.34 | 376 | 502 nm | 84 | 6.90 |

Table 5. Photophysical properties of compound 1 at solid state.

| | HOMO/LUMO[a] (eV) | $T_g^{b)}$ (°C) | $T_d^{b)}$ (°C) | $\lambda_{em}^{c)}$ (nm) | $\Phi_F^{c)}$ (%) | $\tau^{c)}$ (ns) |
|---|---|---|---|---|---|---|
| 1 | −5.18 / −2.34 | 98 | 376 | 502 nm | 84 | 6.90 |

DONOR-ACCEPTOR AGGREGATION-INDUCED EMISSION LUMINOGEN WITH MULTI-STIMULI RESPONSIVE BEHAVIOR

CROSS-REFERENCE TO RELATED APPLICATIONS

This application claims the benefit of priority of U.S. Provisional Application No. 62/920,554, filed on May 6, 2019, the contents of which being hereby incorporated by reference in their entirety for all purposes.

TECHNICAL FIELD

The present disclosure generally relates to aggregation-induced emission luminogens (AIEgen) and methods of preperation and use thereof. More particularly, the present disclosure relates to multi-stimuli responsive AIEgens, methods of use and preparation thereof, and devices and sensors comprising the same.

BACKGROUND

Organisms show various adaptive behaviors and a wide variety of intriguing ways to respond to stimulus from their surrounding environment. For example, *Mimosa pudica* is very sensitive to external stimuli and its leaves quickly close and petiole hangs down in response to tactile stimulations, such as wind, vibration, touch and electrical and mechanical stimulation. Chameleons are well-known for their remarkable ability to instantaneously shift the skin color in response to the surrounding temperature and light stimulus. Such examples are numerous. Today, scientists and engineers are fascinated by these stimuli-responsive behaviors, because investigation of these behaviors may yield new inspiration for developing diverse bio-inspired and smart materials for real-world applications. One common principle learned from these natural creatures is that their unique and complex physiological functions are derived from their selective integration capability of each particular function related to different kinds of specialized cells. And this principle has been efficiently utilized for fabrication of various novel materials by researchers through assembling different structural components with special function into composite systems at the molecular level to achieve multi-functional materials.

At present, there is still an urgent demand for novel smart materials that are able to support more efficient technologies and to achieve a diverse range of practical applications in synthetic material area. By utilizing the same bio-inspired integration strategy, material scientists have developed a wide variety of new smart systems that are able to response to multiple environmental stimuli. For instance, Thayumanavan et al. reported a novel triple stimuli sensitive block copolymer assembly with responses to changes in temperature, pH and redox potential by incorporating an acid-sensitive tetrahydropyran-protected 2-hydroxyethylmethacrylate (THP protected HEMA) and a temperature-sensitive poly(N-isopropylacrylamide) (PNIPAM) with a redox sensitive disulfide linker. Weder's group reported the first supramolecular polymer materials with thermomechanical characteristics of a supramolecular polymer glass by combining mechanoresponsive luminescent compounds with the concept of supramolecular polymerization. Wang and co-workers prepared triple stimulus sensitive supramolecular hydrogel that responded to changes in temperature, light and reduction through the combination of cyclodextrin-based host-guest complexes, poly(N-isopropylacrylamide) chains, azobenzene groups and disulfide bonds. Accordingly, these multiple responsive systems are generally constructed by the integration of multiple components with specific responsive ability. Thus, precise control of each component and time-consuming organic synthesis are required.

Owing to the vacant p-orbital on its central boron atom, triarylborons (TAB) serve as excellent electron acceptors. When conjugated to amine-based electron donor, the resulting donor-acceptor (D-A) small-molecule systems can show unprecedented photophysical and photochemical properties resulting from intramolecular charge transfer (ICT), which have extensive applications in optical storage and memory, optoelectronic and display devices, chemical sensors, security inks and papers, etc. have been developed. While a majority of reported TAB-amine systems only exhibit one specific responsive function, little effort had been placed to explore their versatility and capacity in multifarious applications. In this respect, it would be desirable if multiple individual responsive properties could be integrated into a single small molecule system in a similar way that organisms do without involving tedious synthetic tasks. There is thus a need for simple and versatile small molecule materials with various kinds of environmental responses.

SUMMARY

Provided herein is a versatile TAB-containing compounds with a D-A structure, aggregation-induced emission (AIE) and pronounced ICT effect. This luminogen is sensitive to multiple stimulus, including solvent, temperature, mechanical shearing force, hydrostatic pressure and electric field. Each of them being specifically visualized by a prominent photoluminescence (PL) color change. The compound described herein exhibit multiple responsive properties, including solvatochromic PL, thermochromic PL, mechanochromic PL, electrochromism and electrochromic PL as well as electroluminescence, in a single small molecule system, which is rarely reported. Another unique aspect of the present system is that each responsive behavior has its own specialty.

In a first aspect, provided herein is a compound having the Formula 1:

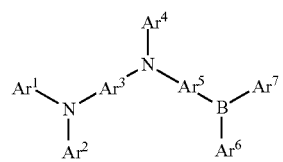

wherein each of $Ar^1$, $Ar^2$, $Ar^3$, $Ar^4$, $Ar^5$, $Ar^6$, and $Ar^7$ is independently selected from the group consisting of aryl and heteroaryl.

In a first embodiment, provided herein is the compound of the first aspect, wherein the compound is represented by the Formula 2:

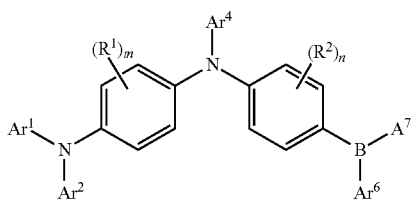

wherein each of m and n is independently 1, 2, 3, or 4;

$R^1$ and $R^2$ for each instance is independently selected from the group consisting of hydrogen, halide, nitrile, nitro, —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, —SO$_2$NR$_2$, alkyl, cycloalkyl, alkenyl, alkynyl, aryl, heterocycloalkyl, and heteroaryl; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; or one instance of $R^1$ and one instance of $R^2$ taken together form a covalent bond; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In a second embodiment, provided herein is the compound of the first aspect, wherein the compound has the Formula 3:

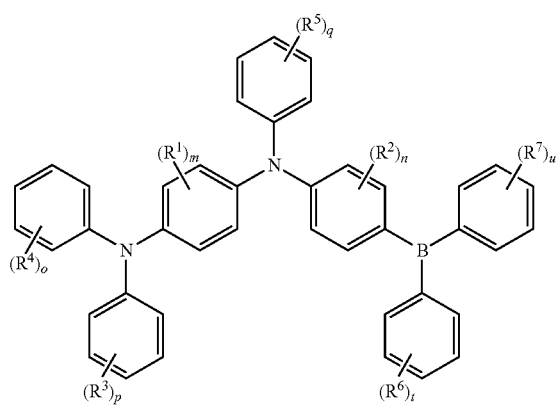

wherein each of m and n is independently 1, 2, 3, or 4;
each of o, p, q, t, and u is independently 1, 2, 3, 4, or 5;

$R^1$ and $R^2$ for each instance is independently selected from the group consisting of hydrogen, halide, nitrile, nitro, —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, —SO$_2$NR$_2$, alkyl, cycloalkyl, alkenyl, alkynyl, aryl, heterocycloalkyl, and heteroaryl; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; or one instance of $R^1$ and one instance of $R^2$ taken together form a covalent bond;

$R^3$, $R^4$, $R^5$, $R^6$, and $R^7$ for each instance is independently selected from the group consisting of hydrogen, halide, nitrile, nitro, —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, —SO$_2$NR$_2$, alkyl, cycloalkyl, alkenyl, alkynyl, aryl, heterocycloalkyl, and heteroaryl; or one instance of $R^4$ and on instance of $R^5$ form a covalent bond; or one instance of $R^3$ and one instance of $R^1$ taken together form a covalent bond; or one instance of $R^3$ and one instance of $R^4$ taken together form a covalent bond; or one instance of $R^1$ and one instance of $R^5$ taken together form a covalent bond; or one instance of $R^2$ and one instance of $R^5$ taken together form a covalent bond; or one instance of $R^2$ and one instance of $R^7$ taken together form a covalent bond; or one instance of $R^6$ and one instance of $R^7$ taken together form a covalent bond; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In a third embodiment, provided herein is the compound of the second embodiment of the first aspect, wherein each of m and n is independently 1 or 2; each of o, p, q, t, and u is independently 1, 2, or 3;

$R^1$ and $R^2$ for each instance is independently selected from the group consisting of hydrogen, halide, nitrile, nitro, —OR, —NR$_2$, alkyl, cycloalkyl, alkenyl, alkynyl, aryl, heterocycloalkyl, and heteroaryl;

$R^3$, $R^4$, $R^5$, $R^6$, and $R^7$ for each instance is independently selected from the group consisting of hydrogen, halide, nitrile, nitro, —OR, —NR$_2$, alkyl, cycloalkyl, alkenyl, alkynyl, aryl, heterocycloalkyl, and heteroaryl; and R for each instance is independently selected from the group consisting of hydrogen, alkyl, aryl, and heteroaryl.

In a fourth embodiment, provided herein is the compound of the first aspect, wherein the compound has the Formula 4:

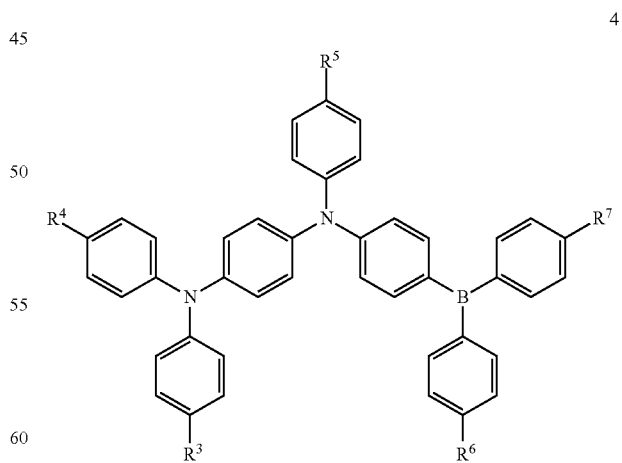

each of $R^3$, $R^4$, $R^5$, $R^6$, and $R^7$ is independently selected from the group consisting of hydrogen, halide, nitrile, nitro, —OR, —NR$_2$, alkyl, cycloalkyl, alkenyl, alkynyl, aryl, heterocycloalkyl, and heteroaryl, wherein R is alkyl, aryl, or heteroaryl.

In a fifth embodiment, provided herein is the compound of the first aspect, wherein the compound has the Formula 5:

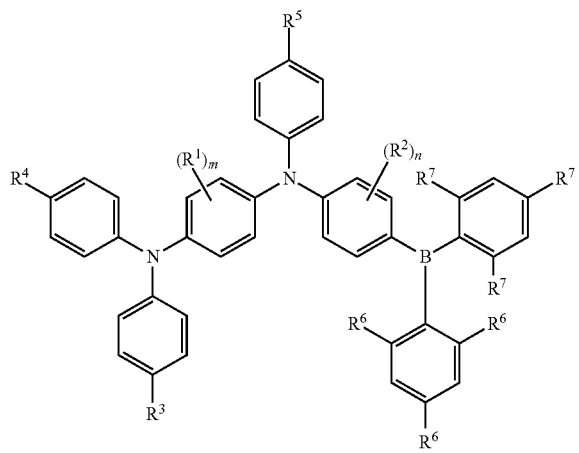

wherein each of m and n is independently 1 or 2;

each of $R^1$ and $R^2$ for each instance is independently selected from the group consisting of hydrogen, halide, nitrile, nitro, —OR, —NR$_2$, —(C=O)R, —(C=O)OR, —(C=O)NR$_2$, —N(R)(C=O)R, —O(C=O)R, —N(R)(C=O)OR, —O(C=O)NR$_2$, alkyl, cycloalkyl, alkenyl, alkynyl, aryl, heterocycloalkyl, and heteroaryl;

$R^3$, $R^4$, $R^5$, $R^6$, and $R^7$ for each instance is independently selected from the group consisting of hydrogen, halide, nitrile, nitro, —OR, —NR$_2$, —(C=O)R, —(C=O)OR, —(C=O)NR$_2$, —N(R)(C=O)R, —O(C=O)R, —N(R)(C=O)OR, —O(C=O)NR$_2$, alkyl, cycloalkyl, alkenyl, alkynyl, aryl, heterocycloalkyl, and heteroaryl; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In a sixth embodiment, provided herein is the compound of the fifth embodiment of the first aspect, wherein each of $R^6$ and $R^7$ for each instance is independently selected from the group consisting of hydrogen, halide, —OR, alkyl, cycloalkyl, alkenyl, alkynyl, aryl, heterocycloalkyl, and heteroaryl.

In a seventh embodiment, provided herein is the compound of the sixth embodiment of the first aspect, wherein each of $R^3$, $R^4$, and $R^5$ are independently selected from hydrogen, —OR, —NR$_2$, alkyl, alkynyl, aryl, and heteroaryl; and R for each instance is independently aryl or heteroaryl.

In an eighth embodiment, provided herein is the compound of the first aspect, wherein the compound has the Formula 6:

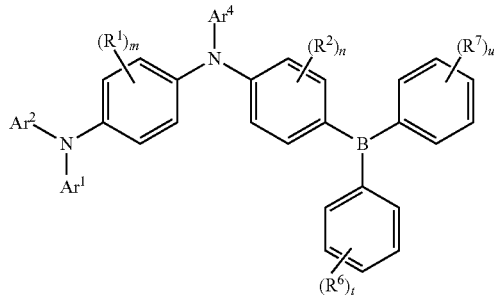

wherein each of m and n is independently 1 or 2;
each of t and u is independently 1, 2, or 3;

$R^1$ and $R^2$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, alkyl, cycloalkyl, alkenyl, alkynyl, aryl, heterocycloalkyl, and heteroaryl; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; or one instance of $R^1$ and one instance of $R^2$ taken together form a covalent bond; or one instance of $R^2$ and one instance of $R^6$ taken together form a covalent bond;

$R^6$ and $R^7$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, alkyl, cycloalkyl, alkenyl, alkynyl, aryl, heterocycloalkyl, and heteroaryl; or one instance of $R^4$ and on instance of $R^5$ form a covalent bond; or one instance of $R^3$ and one instance of $R^1$ taken together form a covalent bond; or one instance of $R^3$ and one instance of $R^4$ taken together form a covalent bond; or one instance of $R^1$ and one instance of $R^5$ taken together form a covalent bond; or one instance of $R^2$ and one instance of $R^5$ taken together form a covalent bond; or one instance of $R^2$ and one instance of $R^7$ taken together form a covalent bond; or one instance of $R^6$ and one instance of $R^7$ taken together form a covalent bond; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In a ninth embodiment, provided herein is the compound of the eighth embodiment of the first aspect, wherein each of $R^1$ and $R^2$ for each instance is independently selected from the group consisting of hydrogen, halide, nitrile, nitro, —OR, —NR$_2$, alkyl, cycloalkyl, alkenyl, alkynyl, aryl, heterocycloalkyl, and heteroaryl;

each of $R^6$ and $R^7$ for each instance is independently selected from the group consisting of hydrogen, halide, nitrile, nitro, —OR, —SR, —NR$_2$, alkyl, cycloalkyl, alkenyl, alkynyl, aryl, heterocycloalkyl, and heteroaryl; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In a tenth embodiment, provided herein is the compound of the eighth embodiment of the first aspect, wherein the compound has Formula 7:

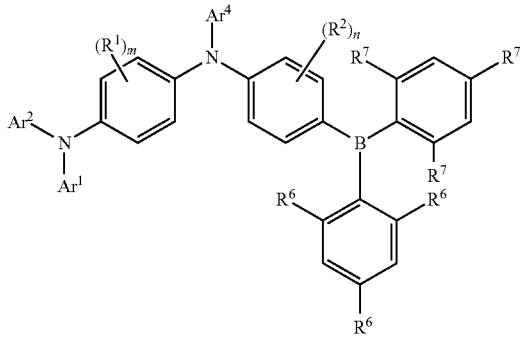

7 wherein each of $R^6$ and $R^7$ for each instance is independently selected from the group consisting of hydrogen, halide, —OR, alkyl, cycloalkyl, alkenyl, alkynyl, aryl, heterocycloalkyl, and heteroaryl.

In an eleventh embodiment, provided herein is the compound of the first aspect, wherein the compound has the Formula 8:

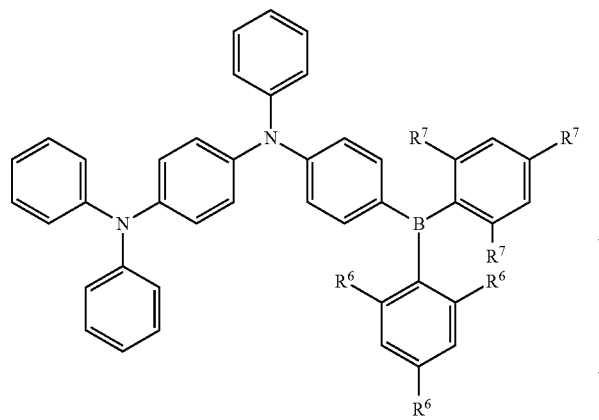

8 wherein each of $R^6$ and $R^7$ is independently selected from hydrogen and alkyl.

In a twelfth embodiment, provided herein is the compound of the eleventh embodiment of the first aspect, wherein each of $R^6$ and $R^7$ is methyl.

In a second aspect, provided herein is a method of preparing the compound of the first aspect, the method comprising: contacting a compound of Formula 1a:

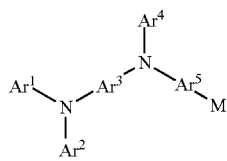

1a wherein each of $Ar^1$, $Ar^2$, $Ar^3$, $Ar^4$, and $Ar^5$ is independently selected from the group consisting of aryl and heteroaryl; and M is lithium, sodium, MgBr, or a Zn species; with a compound of Formula 1b:

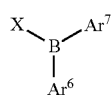

1b wherein each of $Ar^6$, and $Ar^7$ is independently selected from the group consisting of aryl and heteroaryl; and X is a halide; thereby forming the compound of the first aspect.

In a first embodiment of the second aspect, provided herein is the method of the second aspect, wherein the compound of Formula 1a is:

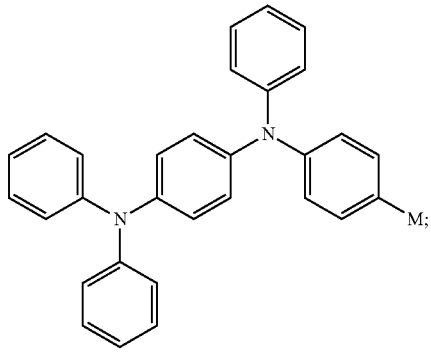

and the compound of Formula 1b is:

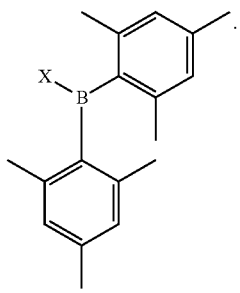

In a third aspect, provided herein is a method for detecting a change in a physical-chemical parameter in a test sample comprising the compound of the first aspect, the method comprising: providing the test sample; measuring the fluorescence emission of the test sample; comparing the measured fluorescence emission of the test sample with the fluorescence emission of a control sample comprising the compound of the first aspect in a ground state; and based on the difference in fluorescence emission between the test sample and the control sample determine whether there is a change in the physical-chemical parameter, wherein the ground state is the fluorescence emission of the compound of the first aspect in the absence of the physical-chemical parameter.

In a first embodiment of the third aspect, provided herein is the method of the third aspect, wherein the physical-chemical parameter is at least one parameter selected from the group consisting of the temperature of the test sample, the sheer force exerted on the test sample, the oxidation state of the test sample, the solvent in the test sample; and the isotropic hydrostatic pressure of the test sample.

In a second embodiment of the third aspect, provided herein is the method of the third aspect, wherein the compound has the formula:

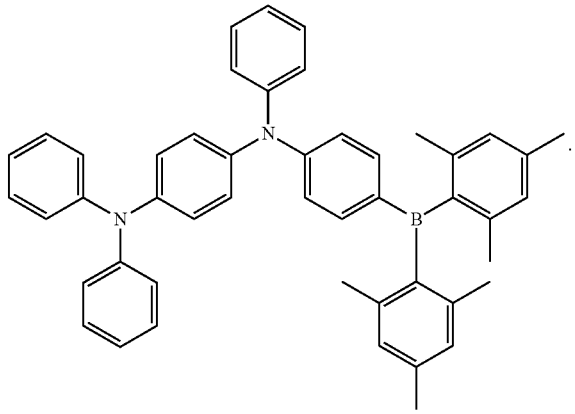 [SMILES: Cc1cc(C)c(B(c2ccc(N(c3ccccc3)c3ccc(N(c4ccccc4)c4ccccc4)cc3)cc2)c2c(C)cc(C)cc2C)c(C)c1]

In a fourth aspect, provided herein is an organic light emitting diode (OLED) comprising the compound of the first aspect.

In a first embodiment of the fourth aspect, provided herein the OLED of the fourth aspect, wherein the compound has the formula:

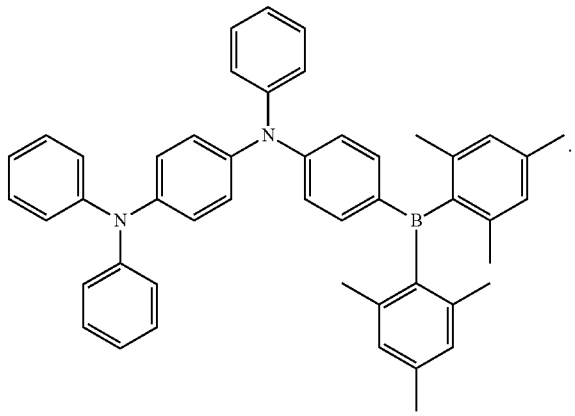 [SMILES: Cc1cc(C)c(B(c2ccc(N(c3ccccc3)c3ccc(N(c4ccccc4)c4ccccc4)cc3)cc2)c2c(C)cc(C)cc2C)c(C)c1]

BRIEF DESCRIPTION OF THE FIGURES

The above and other objects and features of the present disclosure will become apparent from the following description of the disclosure, when taken in conjunction with the accompanying drawings.

FIG. 18 depicts Table 2 showing crystal data and parameters of data collection and refinement for AIEgen 1.

Figure 1:
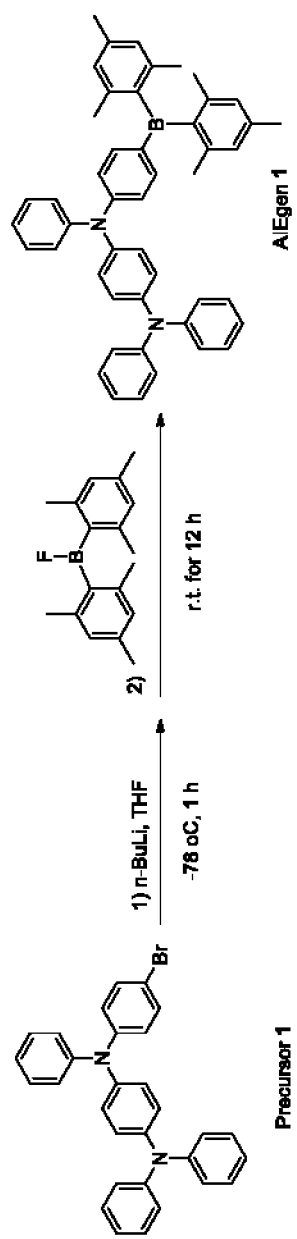
FIG. 1 depicts an exemplary synthetic route to AIEgen 1 in accordance with certain embodiments described herein.

The figures are not necessarily drawn to scale.

DETAILED DESCRIPTION

The present disclosure generally relates to AIE-active small molecules containing TAB and amine units, which are responsive to multiple external stimuli including solvent, temperature, mechanical shearing force, hydrostatic pressure and electric field. More specifically, this new material exhibits solvatochromism and a wide range of thermo-responsive behavior with high upper limit, which can realize the visualization of both marked and subtle environmental polarity change by the dramatically amplified luminescence signal and macroscopic color change. Furthermore, it can respond to anisotropic shearing force and isotropic hydrostatic pressure with remarkable but contrasting luminescence conversion. Meanwhile, it was sensitive to external electric stimulus displaying reversibly three-color switched electrochromism and on-to-off electrochromic photoluminescence. Such properties allow the fabrication of a high-performance non-doped OLED with a high external quantum efficiency of 5.22%. The present system featuring multi-stimulus responsive properties has application in various real-life applications, including the visualization of marked or subtle polarity change, wide-range liquid thermometer, security inks and papers, electroswitchable electrochromic material for information recording, storage device and OLED.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "halo", "halide", or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "aralkyl" is art-recognized and refers to an alkyl group substituted with an aryl group (e.g., an aromatic or heteroaromatic group).

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be optionally substituted as described herein. The aryl ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be optionally substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "optionally substituted" refers to a chemical group, such as alkyl, cycloalkyl, aryl, heteroaryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like The representation "I" as used herein in connection to chemical a group or moiety is intended to represent the covalent bond that the aforementioned chemical group or moiety is covalently bonded to another chemical group or moiety.

The phrase "aggregation-induced emission" or "AIE" as used herein refers to the enhancement of light-emission by a fluorescent compound upon aggregation in the amorphous or crystalline (solid) states of the fluorescent compound, whereas the fluorescent compound exhibits weak or substantially no emission in dilute solutions.

The term "$\lambda_{ex}$" as used herein refers to the excitation wavelength.

The term "$\lambda_{em}$" as used herein refers to the emission wavelength.

Inspired by the distinctive stimuli-responsive behaviors of natural creatures, a simple but versatile class of aggregation-induced emission luminogen (AIEgen) compounds with donor-acceptor structure and pronounced intramolecular charge transfer property, exemplified by AIEgen 1, was developed. The compounds described herein can exhibit solvatochromism and a wide range of thermoresponsive behavior with high upper limit, which can realize the visualization of both marked and subtle environmental polarity change by the dramatically amplified luminescence signal and macroscopic color change. Furthermore, the compounds described herein can respond to numerous environmental or physical-chemical changes, such as anisotropic shearing force and isotropic hydrostatic pressure with remarkable but contrasting luminescence conversion due to the distinct disturbance of the weak intermolecular interactions and charge transfer processes.

The compounds described herein can also be sensitive to external electric stimulus displaying reversibly three-color switched electrochromism and on-to-off electrochromic photoluminescence. Such property allowed the fabrication of high-performance non-doped OLED with a high external quantum efficiency of 5.22%. The present results may offer an efficient guideline for multifunctional molecular design and provide an important step forward in expanding the real-life applications of AIE-active materials.

Provided herein is a compound of Formula 1:

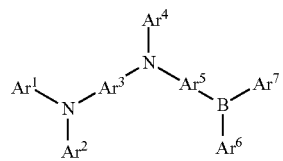

wherein each of $Ar^1$, $Ar^2$, $Ar^3$, $Ar^4$, $Ar^5$, $Ar^6$, and $Ar^7$ is independently selected from the group consisting of aryl and heteroaryl.

In certain embodiments, the $Ar^4$—N nitrogen is covalently bonded to $Ar^5$ in a position in which the lone pair on the said nitrogen is conjugated through the pi system of $Ar^5$ with the boron.

In certain embodiments, each of $Ar^1$, $Ar^2$, $Ar^3$, $Ar^4$, $Ar^5$, $Ar^6$, and $Ar^7$ is independently optionally substituted aryl or heteroaryl. Each of $Ar^1$, $Ar^2$, $Ar^3$, $Ar^4$, $Ar^5$, $Ar^6$, and $Ar^7$ can independently be optionally substituted with a substituent selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, alkyl, cycloalkyl, alkenyl, alkynyl, aryl, heterocycloalkyl, and heteroaryl, wherein R is hydrogen, alkyl, cycloalkyl, alkenyl, alkynyl, aryl, heterocycloalkyl, and heteroaryl; or two instances of R taken together form a 3-6 membered heterocycloalkyl. Each of $Ar^1$, $Ar^2$, $Ar^3$, $Ar^4$, $Ar^5$, $Ar^6$, and $Ar^7$ can independently be optionally substituted with 1, 2, 3, 4, 5, 6, 7, 8, 9, or 10 substituents.

In certain embodiments, each of $Ar^1$, $Ar^2$, $Ar^3$, $Ar^4$, $Ar^5$, $Ar^6$, and $Ar^7$ is independently optionally substituted phenyl.

In certain embodiments, the compound has the Formula 2:

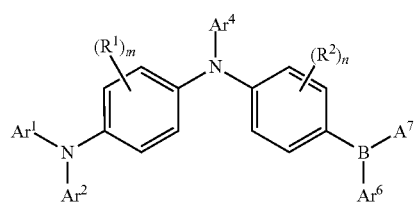

wherein each of m and n is independently 1, 2, 3, or 4;

$R^1$ and $R^2$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, alkyl, cycloalkyl, alkenyl, alkynyl, aryl, heterocycloalkyl, and heteroaryl; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; or one instance of $R^1$ and one instance of $R^2$ taken together form a covalent bond; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In certain embodiments of the compound of Formula 2, each of m and n is 1 or 2; and $R^1$ and $R^2$ for each instance is independently selected from the group consisting of hydrogen, halide, nitrile, nitro, —OR, —SR, —NR$_2$, alkyl, cycloalkyl, alkenyl, alkynyl, aryl, heterocycloalkyl, and heteroaryl.

In certain embodiments of the compound of Formula 2, each of $Ar^1$, $Ar^2$, $Ar^4$, $Ar^6$, and $Ar^7$ is independently aryl. In certain embodiments, each of $Ar^1$, $Ar^2$, $Ar^4$, $Ar^6$, and $Ar^7$ is independently optionally substituted phenyl.

In certain embodiments, the compound has the Formula 3:

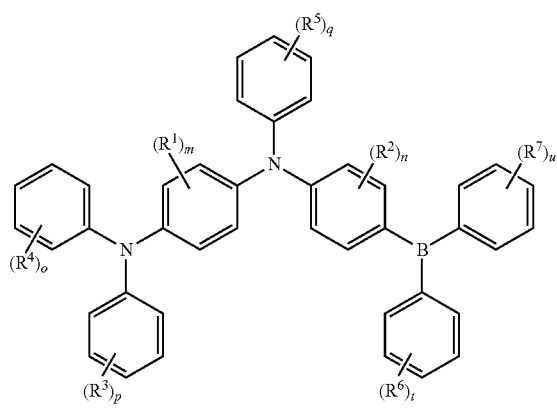

3 wherein each of m and n is independently 1, 2, 3, or 4; each of o, p, q, t, and u is independently 1, 2, 3, 4, or 5;

$R^1$ and $R^2$ for each instance is independently selected from the group consisting of hydrogen, halide, nitrile, nitro, —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, —SO$_2$NR$_2$, alkyl, cycloalkyl, alkenyl, alkynyl, aryl, heterocycloalkyl, and heteroaryl; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; or one instance of $R^1$ and one instance of $R^2$ taken together form a covalent bond;

$R^3$, $R^4$, $R^5$, $R^6$, and $R^7$ for each instance is independently selected from the group consisting of hydrogen, halide, nitrile, nitro, —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, —SO$_2$NR$_2$, alkyl, cycloalkyl, alkenyl, alkynyl, aryl, heterocycloalkyl, and heteroaryl; or one instance of $R^4$ and on instance of $R^5$ form a covalent bond; or one instance of $R^3$ and one instance of $R^1$ taken together form a covalent bond; or one instance of $R^3$ and one instance of $R^4$ taken together form a covalent bond; or one instance of $R^1$ and one instance of $R^5$ taken together form a covalent bond; or one instance of $R^2$ and one instance of $R^5$ taken together form a covalent bond; or one instance of $R^2$ and one instance of $R^7$ taken together form a covalent bond; or one instance of $R^6$ and one instance of $R^7$ taken together form a covalent bond; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In certain embodiments of the compound of Formula 3, each of m and n is 1; and each of o, p, q, t, and u is 1.

In certain embodiments, the compound has Formula 3a:

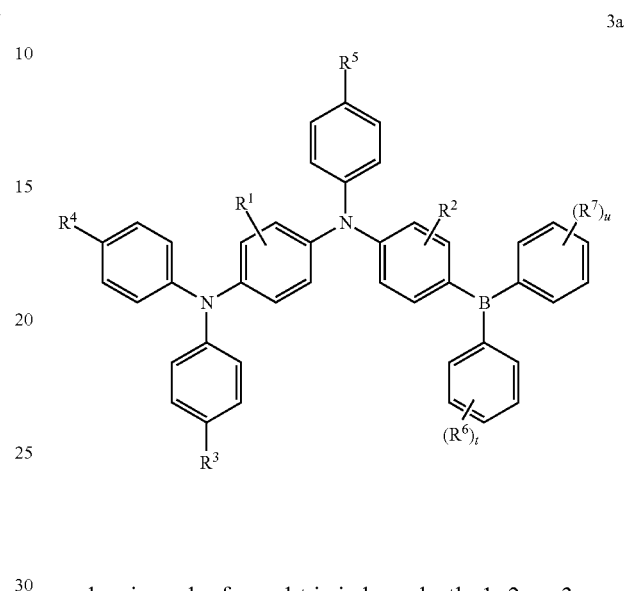

3a wherein each of u and t is independently 1, 2, or 3;

$R^1$, $R^2$, $R^3$, $R^4$, $R^5$, $R^6$, and $R^7$ for each instance is independently selected from the group consisting of hydrogen, halide, nitrile, nitro, —OR, —SR, —NR$_2$, —(C═O)R, —(C═O)OR, —(C═O)NR$_2$, —N(R)(C═O)R, —O(C═O)R, —N(R)(C═O)OR, —O(C═O)NR$_2$, —SO$_2$R, —SO$_2$NR$_2$, alkyl, cycloalkyl, alkenyl, alkynyl, aryl, heterocycloalkyl, and heteroaryl; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In certain embodiments of the compound of Formula 3a, R for each instance is independently selected from the group consisting of hydrogen, alkyl, cycloalkyl, alkenyl, alkynyl, aryl, heterocycloalkyl, and heteroaryl.

In certain embodiments of the compound of Formula 3a, each of $R^1$ and $R^2$ is independently selected from the group consisting of hydrogen, halide, nitrile, nitro, —OR, —NR$_2$, alkyl, cycloalkyl, alkenyl, alkynyl, aryl, heterocycloalkyl, and heteroaryl. In certain embodiments of the compound of Formula 3a, $R^1$ and $R^2$ are hydrogen.

In certain embodiments of the compound of Formula 3a, each of $R^3$, $R^4$, $R^5$, $R^6$, and $R^7$ is independently selected from the group consisting of hydrogen, halide, nitrile, nitro, —OR, —NR$_2$, alkyl, cycloalkyl, alkenyl, alkynyl, aryl, heterocycloalkyl, and heteroaryl.

In certain embodiments of the compound of Formula 3a, $R^1$ and $R^2$ are hydrogen; $R^3$, $R^4$, $R^5$, $R^6$, and $R^7$ for each instance is independently selected from hydrogen, —OR, —SR, —NR$_2$, alkyl, cycloalkyl, alkenyl, alkynyl, aryl, heterocycloalkyl, and heteroaryl; and R for each instance is independently selected from the group consisting of hydrogen, alkyl, cycloalkyl, alkenyl, alkynyl, aryl, heterocycloalkyl, and heteroaryl.

In certain embodiments, the compound has Formula 4:

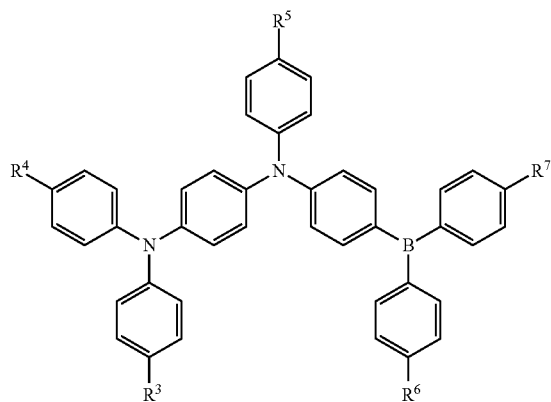

each of $R^3$, $R^4$, $R^5$, $R^6$, and $R^7$ is independently selected from the group consisting of hydrogen, halide, nitrile, nitro, —OR, —NR$_2$, alkyl, cycloalkyl, alkenyl, alkynyl, aryl, heterocycloalkyl, and heteroaryl, wherein R is alkyl, aryl, or heteroaryl.

In certain embodiments of the compound of Formula 4, each of $R^3$, $R^4$, $R^5$, $R^6$, and $R^7$ is independently selected from the group consisting of hydrogen, —OR, alkyl, alkenyl, alkynyl, aryl, and heteroaryl, wherein R is alkyl, aryl, or heteroaryl.

In certain embodiments, the compound has Formula 5:

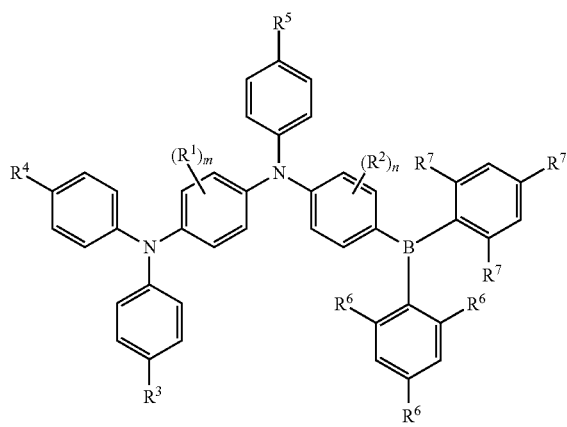

wherein each of m and n is independently 1 or 2;
each of $R^1$ and $R^2$ is independently selected from the group consisting of hydrogen, halide, nitrile, nitro, —OR, —NR$_2$, —(C=O)R, —(C=O)OR, —(C=O)NR$_2$, —N(R)(C=O)R, —O(C=O)R, —N(R)(C=O)OR, —O(C=O)NR$_2$, alkyl, cycloalkyl, alkenyl, alkynyl, aryl, heterocycloalkyl, and heteroaryl;
each of $R^3$, $R^4$, $R^5$, $R^6$, and $R^7$ is independently selected from the group consisting of hydrogen, halide, nitrile, nitro, —OR, —NR$_2$, —(C=O)R, —(C=O)OR, —(C=O)NR$_2$, —N(R)(C=O)R, —O(C=O)R, —N(R)(C=O)OR, —O(C=O)NR$_2$, alkyl, cycloalkyl, alkenyl, alkynyl, aryl, heterocycloalkyl, and heteroaryl; and
R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In certain embodiments of the compound has Formula 5, each of $R^1$ and $R^2$ for each instance is independently selected from the group consisting of hydrogen, halide, nitrile, nitro, alkyl, cycloalkyl, alkenyl, alkynyl, aryl, heterocycloalkyl, and heteroaryl.

In certain embodiments of the compound of Formula 5, each of $R^3$, $R^4$, $R^5$, $R^6$, and $R^7$ is independently selected from the group consisting of hydrogen, halide, nitrile, nitro, —OR, —NR$_2$, alkyl, cycloalkyl, alkenyl, alkynyl, aryl, heterocycloalkyl, and heteroaryl.

In certain embodiments of the compound has Formula 5, each of $R^6$ and $R^7$ is hydrogen, alkyl, cycloalkyl, aryl, or heteroaryl.

In certain embodiments of the compound has Formula 5, each of $R^1$ and $R^2$ is hydrogen; each of $R^3$, $R^4$, and $R^5$ is independently selected from the group consisting of hydrogen, halide, nitrile, nitro, —OR, —NR$_2$, alkyl, cycloalkyl, alkenyl, alkynyl, aryl, heterocycloalkyl, and heteroaryl; and each of $R^6$ and $R^7$ is hydrogen, alkyl, cycloalkyl, aryl, or heteroaryl.

In certain embodiments, the compound has Formula 6:

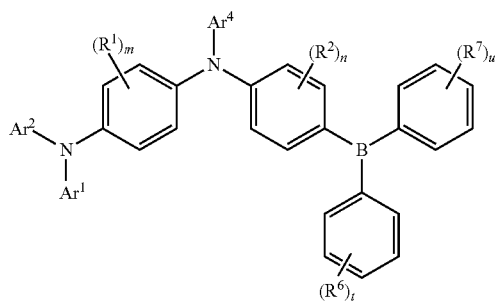

wherein each of m and n is independently 1 or 2;
each of t and u is independently 1, 2, or 3;
$R^1$ and $R^2$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, alkyl, cycloalkyl, alkenyl, alkynyl, aryl, heterocycloalkyl, and heteroaryl; or two instance of $R^1$ taken together form a 5-6 membered cycloalkyl, heterocycloalkyl, aryl, or heteroaryl; or two instance of $R^2$ taken together form a 5-6 membered cycloalkyl, heterocycloalkyl, aryl, or heteroaryl; or one instance of $R^1$ and one instance of $R^2$ taken together form a covalent bond; or one instance of $R^2$ and one instance of $R^6$ taken together form a covalent bond;

$R^6$ and $R^7$ for each instance is independently selected from the group consisting of hydrogen, halide, nitrile, nitro, —OR, —SR, —NR$_2$, —(C=O)R, —(C=O)OR, —(C=O)NR$_2$, —N(R)(C=O)R, —O(C=O)R, —N(R)(C=O)OR, —O(C=O)NR$_2$, —SO$_2$R, —SO$_2$NR$_2$, alkyl, cycloalkyl, alkenyl, alkynyl, aryl, heterocycloalkyl, and heteroaryl; or one instance of $R^4$ and on instance of $R^5$ form a covalent bond; or one instance of $R^3$ and one instance of $R^1$ taken together form a covalent bond; or one instance of $R^3$ and one instance of $R^4$ taken together form a covalent bond; or one instance of $R^1$ and one instance of $R^5$ taken together form a covalent bond; or one instance of $R^2$ and one instance of $R^5$ taken together form a covalent bond; or one instance of $R^2$ and one instance of $R^7$ taken together form a covalent bond; or one instance of $R^6$ and one instance of $R^7$ taken together form a covalent bond; and R for each instance is independently selected from the group consisting of hydrogen, alkyl, cycloalkyl, alkenyl, alkynyl, aryl, heterocycloalkyl, and heteroaryl; or two instances of R taken together form a 3-6 membered heterocycloalkyl.

In certain embodiments, the compound has Formula 7:

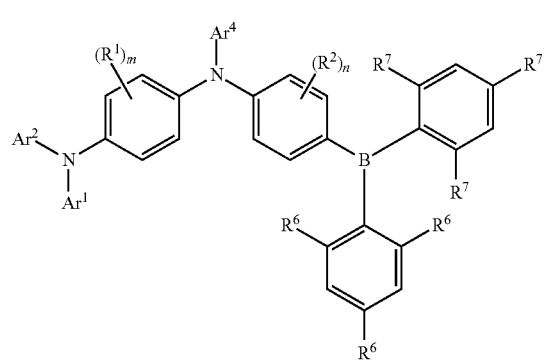

7 wherein each of m and n is independently 1 or 2; each of $Ar^1$, $Ar^2$, and $Ar^4$ is independently selected from the group consisting of aryl and heteroaryl; $R^1$ and $R^2$ for each instance is independently selected from the group consisting of hydrogen alkyl, cycloalkyl, alkenyl, alkynyl, aryl, heterocycloalkyl, and heteroaryl; each of $R^6$ and $R^7$ for each instance is independently selected from the group consisting of hydrogen, halide, —OR, alkyl, cycloalkyl, alkenyl, alkynyl, aryl, heterocycloalkyl, and heteroaryl.

In certain embodiments of the compound of Formula 7, $Ar^1$, $Ar^2$, and $Ar^4$ is independently optionally substituted phenyl. In certain embodiments of the compound of Formula 7, each $R^1$ and $R^2$ is hydrogen; each of $Ar^1$, $Ar^2$, and $Ar^4$ is independently optionally substituted phenyl; and each of $R^6$ and $R^7$ for each instance is independently selected from the group consisting of hydrogen, alkyl, aryl, and heteroaryl.

In certain embodiments, the compound has the Formula 8:

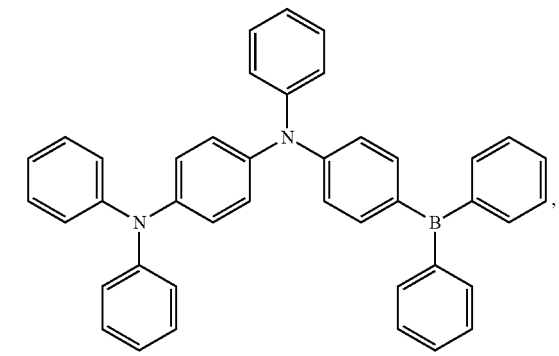

8 wherein each of $R^6$ and $R^7$ is independently selected from hydrogen and alkyl. In certain embodiments, each of $R^6$ and $R^7$ is $C_1$-$C_6$ alkyl. In certain embodiments, each of $R^6$ and $R^7$ is methyl.

In certain embodiments, the compound is selected from the group consisting of:

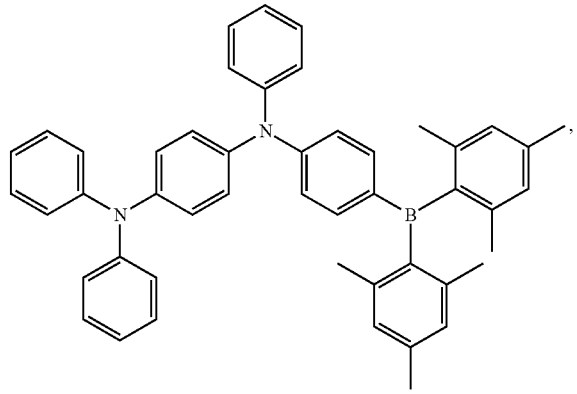

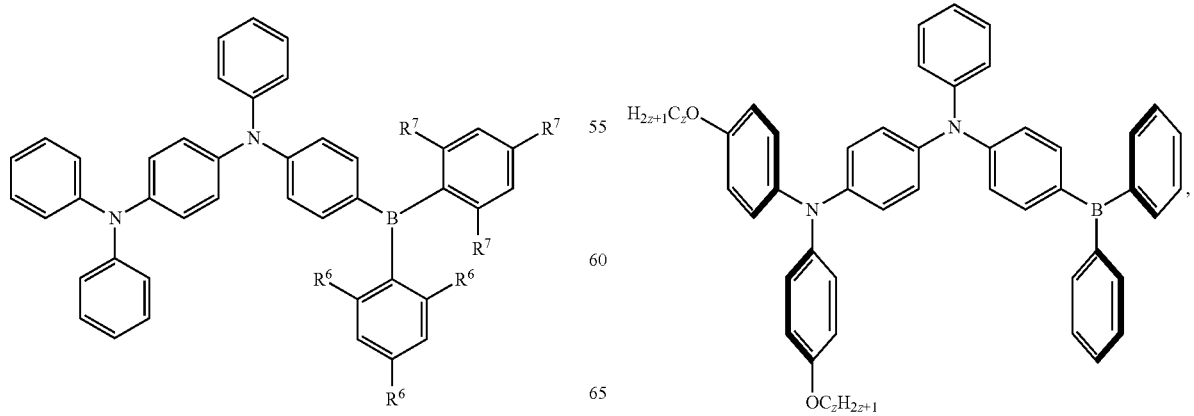

-continued

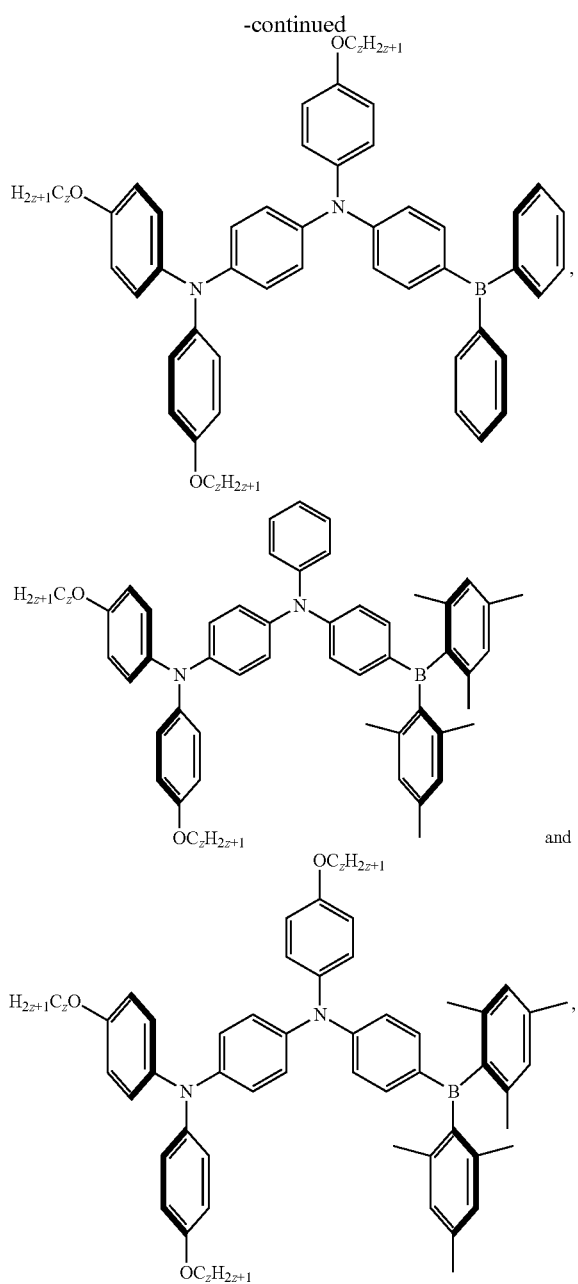

and wherein z is 0-12.

The compounds described herein can be covalently conjugated to a targeting agent. The targeting agent can be an antibody, an antibody fragment (such as Fab, Fab', F(ab')$_2$, and Fv), single chain (ScFv)) a peptide, an aptamer, or a small molecule that is capable of selectively binding to a target of interest, such as a carbohydrate, polynucleotide, lipid, polypeptide, protein, small molecule, cellular receptor, etc.

The compound described herein can be directly attached to the targeting agent or attached to the targeting agent via a chemical linker. In instances where the compound described herein is attached to the targeting agent via a linker, any linker in the art can be used to attach the compound described herein and the targeting agent. The selection of the linker is well within the skill of a person skilled in the art. Exemplary linkers include, but are not limited to polyethylene glycol linkers, alkyl amides, alkyl esters, alkyl sulfonamides, alkyl sulfones, alkanes, aryl amides, aryl esters, aryl sulfonamides, aryl sulfones, aryl, and combinations thereof. The linker can be covalently attached to the targeting agent by an amide bond, ester bond, sulfone bond, sulfur bond, a bond to a trizole, urea bond, ether bond or the like.

In certain embodiments, the compounds described herein comprise a linker. The linker can be covalently attached to the compounds described herein at any at position of the compound subject to the rules of valency. In certain embodiments of any of the compounds described herein, $R^1$, $R^2$, $R^3$, $R^4$, $R^5$, $R^6$, or $R^7$ is the linker, wherein the linker is represented by the formula: -Q$^1$(CH$_2$)$_v$Y$^2$, wherein v is a whole number selected between 0-10; Q$^1$ is a bond, —O—, —(C=O)O—, —O(C=O)—, —(C=O)NH—, or —NH(C=O)—; and Y$^2$ is —NH$_2$, —OH, —SH, —CO$_2$H, alkyne, azide, or N-maleimide; or the linker is represented by the formula: —(OCH$_2$CH$_2$)$_v$Y$^2$ or —(CH$_2$CH$_2$)$_v$(CH$_2$)$_w$Y$^2$, wherein each of v and w is independently 1-10; and Y$^2$ is —NH$_2$, —OH, —SH, —CO$_2$H, alkyne, azide, or N-maleimide.

The compounds described herein can be readily prepared using well known organic synthetic methodologies. Synthetic chemists can devise numerous synthetic routes for preparing the compound of Formula 1 using retrosynthetic analysis.

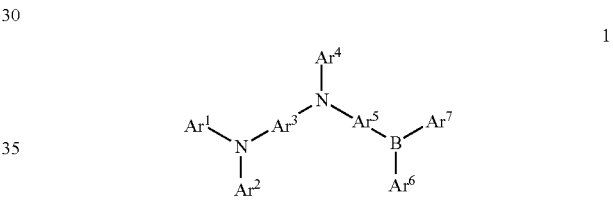

1

In one exemplary approach the carbon boron covalent bond can be formed in the final step of the synthetic methodology as shown below:

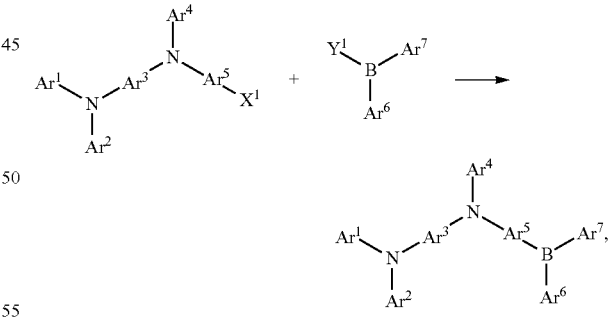

wherein Ar$^1$, Ar$^2$, Ar$^3$, Ar$^4$, Ar$^5$, Ar$^6$, and Ar$^7$ are as defined herein.

This synthetic transformation can be accomplished any number of ways. For example, metal catalyzed (e.g., palladium) cross coupling of a tetraryl diborane (e.g., wherein Y$^1$=—B(Ar$^6$)(Ar$^7$)) and a suitably functionalized aryl or heteroaryl halide, tosylate, mesylate, trifluormesylate, or other suitable leaving group (e.g., wherein X$^1$=halide, tosylate, mesylate, trifluormesylate, and the like). This approach suffers from the waste of half the tetraryldiborane, as only one diaryl borane is coupled in the reaction.

Alternatively, a substitution reaction can be used to couple an aryl or heteroaryl active metal (e.g., wherein $X^1$ is Li, Na, MgBr, or a zinc species, such as Znalkyl, Znhalide, or

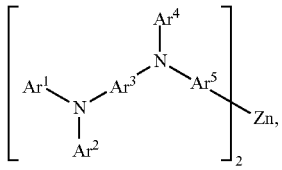

and $Y^1$ is a leaving group (e.g., wherein $Y^1$ is halide or alkoxide).

In another aspect, provided herein is a method for preparing the compound of Formula 1, the method comprising: the method comprising: contacting a compound of Formula 1a:

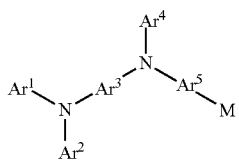

1a wherein each of $Ar^1$, $Ar^2$, $Ar^3$, $Ar^4$, and $Ar^5$ is independently selected from the group consisting of aryl and heteroaryl; and M is lithium, sodium, MgBr, or a Zn species; with a compound of Formula 1b:

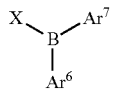

1b wherein each of $Ar^6$, and $Ar^7$ is independently selected from the group consisting of aryl and heteroaryl; and X is a halide; thereby forming the compound Formula 1.

Any of the compounds described herein can be prepared in a similar fashion. For example, AIEgen 1 can be prepared when the compound of Formula 1a is:

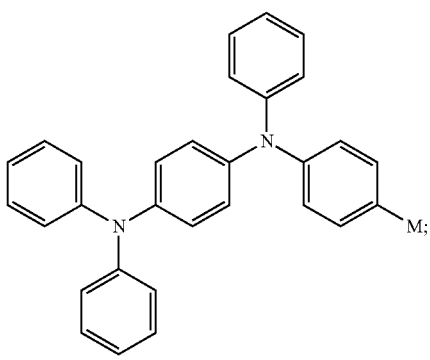

and the compound of Formula 1b is:

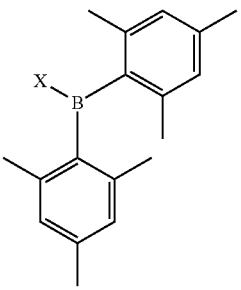

Figure 2:
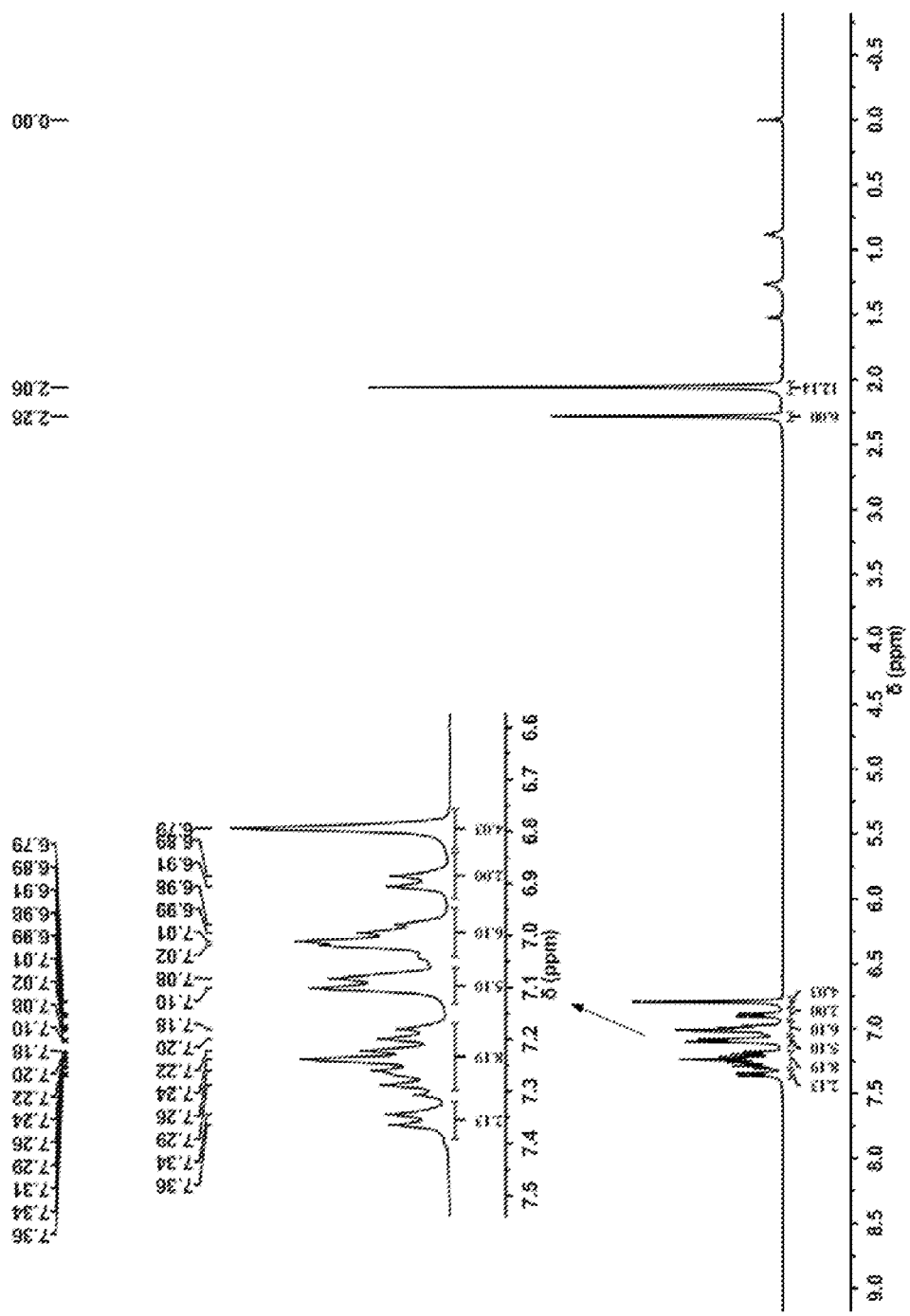
FIG. 2 depicts the $^1$H NMR spectrum of AIEgen 1 in CDC$_3$.
Figure 3:
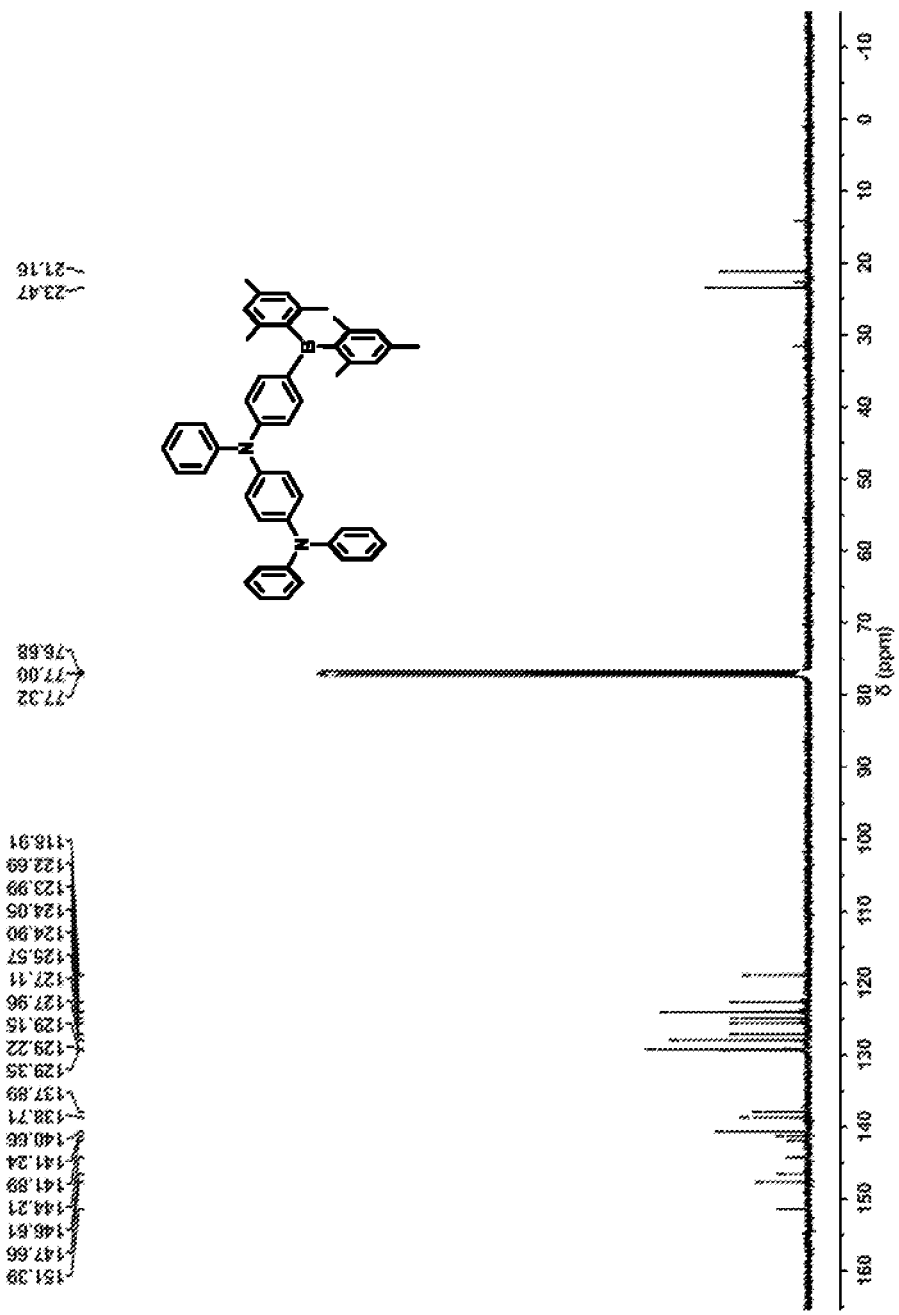
FIG. 3 depicts the $^{13}$C NMR spectrum of AIEgen 1 in CDC$_3$.
Figure 4:
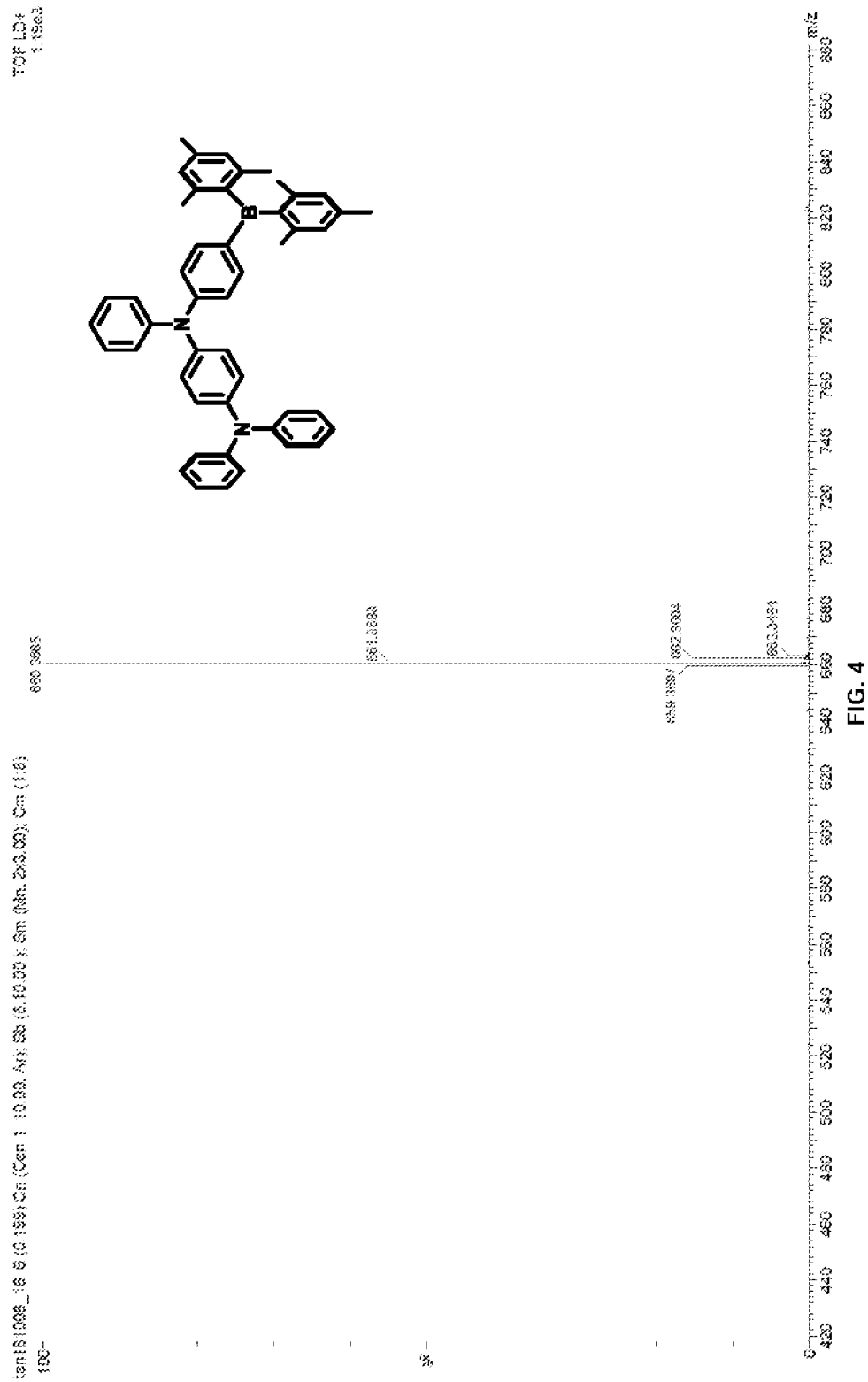
FIG. 4 depicts the HR-MS spectrum of AIEgen 1.
Figures 7, 8:
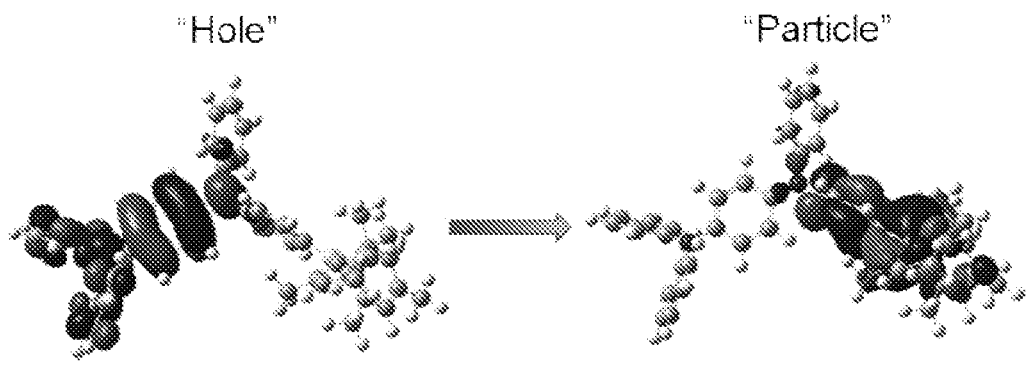
FIG. 7 depicts Table 1 that includes photophysical properties of AIEgen 1 in different solvents. [a] $v_a$ and $v_f$ are the UV and PL peaks in different solvents, respectively; [b] Stokes shift in different solvents; [c] Orientation polarization; [d] Absolute fluorescence quantum yield.
FIG. 8 depicts the natural transition orbitals (NTO) of the first singlet excited state. The contribution of the electronic transition to the first singlet excitation state is about 99%.

An exemplary synthesis of AIEgen 1 is depicted in FIG. 1 in which the Precursor 1 undergoes metal-halogen exchange to generate a reactive aryl-lithium intermediate, compound of Formula 1a, which then undergoes a substitution reaction with dimesitylboron fluoride thereby forming AIEgen 1. As detailed in the examples below, AIEgen 1 was facilely prepared in a high yield of 79% through a simple one-step reaction along the synthetic route as presented in FIG. 1 in the Supporting Information. The product was well characterized by NMR and high-resolution mass spectroscopy with satisfactory results (FIGS. 2-4). The structure of 1 was further confirmed by single crystal X-ray diffraction (details see below) and the associated data was summarized in Table 1 (FIG. 7).

A person of ordinary skill in the art can readily conceive of the chemical structures of starting materials for preparing any of the compounds described herein based on the teachings provided herein and general knowledge in the art.

The step of contacting the compound of Formula 1a and the compound of Formula 1b can be conducted in relatively unreactive aprotic solvents. Exemplary solvents include, but are not limited to ethers, aromatics, and combinations thereof. Suitable ethers include, but are not limited to diethyl ether, tetrahydrofuran, 2-methyltetrahydrofuran, tetrahydropyran, dioxane, 1,2,-dimethoxyether (DME), tert-butyl methyl ether, and the like. Suitable aromatics include, but are not limited to, benzene, toluene, xylenes, and the like.

The step of contacting the compound of Formula 1a and the compound of Formula 1b can be first be conducted at a temperature in the range of −100° C. to 20° C. and then optionally be allowed to warm to room temperature. In certain embodiments, the step of contacting the compound of Formula 1a and the compound of Formula 1b can first be conducted at a temperature in the range of −100° C. to 20° C.; −100° C. to 10° C.; −100° C. to 0° C.; −90° C. to 0° C.; −80° C. to 0° C.; −80° C. to −10° C.; −80° C. to −20° C.; −80° C. to −30° C.; or −80° C. to −40° C.; −100° C. to 40° C.; −60° C. to 40° C.; −100° C. to 50° C.; −90° C. to 80° C.; and then allowed to optionally warm to room temperature.

As described in greater detail in this disclosure, the compounds described herein can exhibit multi-stimuli responsive fluorescent emissions. Such properties enable the use of the compound described herein as sensors that are responsive to changes in a physical-chemical parameter.

Thus in another aspect, provided herein is a method for detecting a change in a physical-chemical parameter in a test sample comprising the compound described herein, the method comprising: providing the test sample; measuring the fluorescence emission of the test sample; comparing the measured fluorescence emission of the test sample with the fluorescence emission of a control sample comprising the compound described herein in a ground state; and based on the difference in fluorescence emission between the test sample and the control sample determine whether there is a change in the physical-chemical parameter, wherein the ground state is the fluorescence emission of the compound described herein in the absence of the physical-chemical parameter.

In certain embodiments, the physical-chemical parameter is at least one parameter selected from the group consisting of the temperature of the test sample, the sheer force exerted on the test sample, the oxidation state of the test sample, the solvent in the test sample; the solvent composition of the test sample; and the isotropic hydrostatic pressure of the test sample.

The multi-stimuli responsive emissive behavior of the compounds described herein have numerous applications, such as in liquid thermometers, security inks and papers, electroswitchable electrochromic material for information recording, storage devices and OLED.

The difference in fluorescence emission can be a change in the emission wavelength, change in emission intensity, or a combination thereof.

The EL properties of the compounds described herein can be particularly useful in the fabrication of luminescent devices, such as variously configured OLEDs. OLEDs that can be fabricated using the compound of Formula I include from very simple structures having a single anode and cathode (e.g., monolayer OLEDs) to more complex devices, such as 2-layer or multilayer heterostructure configurations.

In certain embodiments, the OLED comprises an anode, a cathode, and a light emissive layer disposed between the anode and the cathode. In certain embodiments the OLED further comprises a hole-transport layer.

Figures 28, 29:
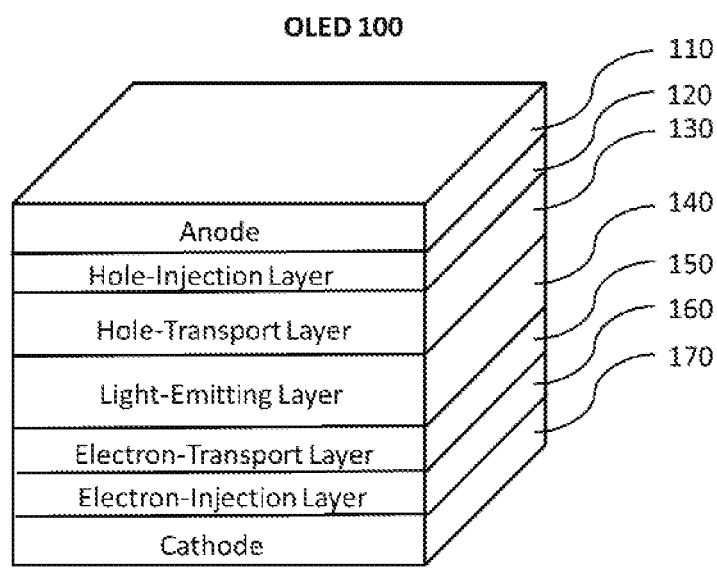
FIG. 28 depicts Table 5. Photophysical properties of AIEgen 1 at solid state. $^{a)}$ The LUMO energy level was calculated from the HOMO energy level according to the equation HOMO=LUMO–E$_g$ (HOMO=–(4.8+E$_{ox}^{onset}$) eV) and E$_g$ was calculated from the low-energy absorption onset in the absorption spectra according to the equation E$_g$=1240/λ$_{onset}$.[4] $^{b)}$ Solid state. $^{c)}$ Vacuum-deposited on a quartz substrate.
FIG. 29 depicts an exemplary OLED according to certain embodiments described herein.
Figure 30:
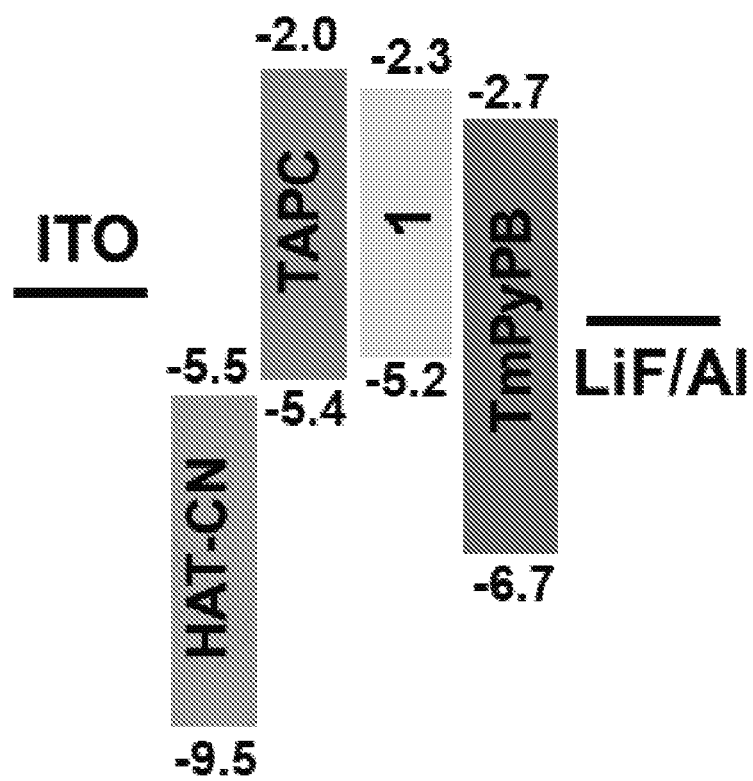
FIG. 30 depicts the energy levels of an OLED comprising AIEgen 1 (labeled 1 in the Figure) in accordance with certain embodiments described herein.

In certain embodiments, the OLED has the structure shown in FIG. 29. OLED 100 contains an anode 110, a hole-injection layer 120, a hole-transport layer 130, a light-emitting layer 140, an electron-transport layer 150, an electron-injection layer 160 and a cathode 170. The light-emitting layer 140 can comprises the compound of Formula I as a thin film. In some other embodiments, there are optional layers on either side of the light-emitting layer 140.

In certain embodiments, the electron-injection layer 160 can be subdivided into two or more sublayers (not shown). In one illustrative example of the OLED, the electron-injection layer 170 is further divided into two sublayers, a first electron-injection layer adjacent to the electron-transport layer 150 and a second electron-injection layer located between the first electron-injection layer and the cathode.

In certain embodiments, the hole-injection layer 120 can be subdivided into two or more sublayers (not shown). In one illustrative example of the OLED device, the hole-injection layer 120 is further divided into two sublayers, a first hole-injection layer adjacent to the hole-transport layer 130 and a second hole-injection layer located between the first hole-injection layer and the anode.

In certain embodiments, there is a hole-blocking layer between the light-emitting layer 140 and the electron-transport layer 150 (not shown).

The OLED can be configured such that the EL emission of the anode or alternatively through the cathode. When the EL emission occurs through the anode, the anode 110 should be transparent or substantially transparent to the emitted wavelengths. Commonly used transparent anode materials include, but are not limited to, indium-tin oxide (ITO), indium-zinc oxide (IZO) tin oxide, aluminum- or indium-doped zinc oxide, magnesium-indium oxide, nickel-tungsten oxide, gallium nitride, zinc selenide, zinc sulfide. When the EL emission occurs through the cathode 170, the optical properties of the anode 110 are immaterial and any conductive material, transparent, opaque or reflective can be used. Example conductors for this application include, but are not limited to, gold, iridium, molybdenum, palladium, and platinum.

The anode 110 can be deposited any suitable way such as evaporation, sputtering, chemical vapor deposition, or electrochemical processes. Anodes can be patterned using, e.g., conventional photolithographic processes.

The hole-injection material can serve to facilitate injection of holes into the hole-transport layer 130. The hole-injection layer 120 can be formed of any hole-injection material including those that are commonly used. Non-limiting examples of hole-injection materials are N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl-N,N'-diphenylbenzidine) (NPB), 4,4',4"-tris(N,N-diphenylamino)triphenylamine (TDATA), 4,4',4"-tris-(N-(naphthylen-2-yl)-N-phenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrene-sulfonate) (PANI/PSS), tetracyanoquinonedimethane (TCNQ), 2,3,5,6-tetrafluoro-tetracyano-1,4-benzoquinonedimethane (F4-TCNQ) and additional hole-injection materials, such as dipyrazino[2,3-f:2',3'-h]quinoxalinehexacarbonitrile (HATCN) are described in U.S. Publication 2004/0113547 A1 and U.S. Pat. No. 6,720,573.

The hole-injection material can be deposited using any suitable conventional method known in the art including, but not limited to, vacuum deposition, spin coating, printing, print screening, spraying, painting, doctor-blading, slot-die coating, and dip coating.

The hole-transport layer 130 can be formed of any hole-transport material including those that are commonly used. Non-limiting examples of suitable known hole-transport materials are carbazole derivatives, such as N-phenylcarbazole or polyvinylcarbazole, N,N'-bis(3-methylphenyl-N,N'-diphenyl-[1,1-biphenyl]-4,4'-diamine (TPD), 4,4',4"-tris(N-carbazolyl)triphenylamine (TCTA), (4,4'-(cyclohexane-1,1-diyl)bis(N,N-di-p-tolylaniline)) (TAPC), and N,N'-di(1-naphthyl-N,N'-diphenylbenzidine) (NPB).

The hole-transport material can be deposited using any suitable conventional method known in the art including, but not limited to, vacuum deposition, spin coating, printing, print screening, spraying, painting, doctor-blading, slot-die coating, and dip coating.

The light-emitting layer 140 can comprise a substantially pure thin film comprising a compound of Formula 1 or a host matrix doped with a compound of Formula I. In instance in which the light-emitting layer comprises a host matrix, the host matrix can be any host matrix material known in the art. Non-limiting examples of host matrix materials include bis(4-(3,6-diphenyl-9H-carbazol-9-yl)phenyl)methanone, 9-(4-(4,6-diphenylpyrimidin-2-yl)phenyl)-9H-carbazole, 4-(4-diphenylaminophenyl)diphenylsulfone, 9-(9-phenyl-9H-carbazol-3-yl)-9-p-tolyl-9H-fluorene-3-carbonitrile, 3,5-di(9H-carbazol-9-yl)benzonitrile, 2-(diphenylphosphinyl)-spiro[9H-fluorene-9,9'-quino[3,2,1-kl]phenoxazine], 2,8-bis(diphenylphosphoryl)dibenzo[b,d]thiophene, 4,4'-bis(carbazol-9-yl)biphenyl, 4,4',4"-tris(carbazol-9-yl)triphenylamine, 2,6-bis(9,9-diphenylacridin-10(9H)-yl)pyrazine, 1,3-bis(carbazol-9-yl)benzene, 4,4',4"-Tris(carbazol-9-yl)triphenylamine, 4,4'-bis(carbazol-9-yl)biphenyl, 9-(4-tert-butylphenyl)-3,6-bis(triphenylsilyl)-9H-carbazole, 1,3,5-tri

[(3-pyridyl)-phen-3-yl]benzene, 2,8-bis(diphenylphosphoryl)dibenzo[b,d]thiophene, bis[2-(diphenylphosphino)phenyl]ether oxide, 2,6-di(9H-carbazol-9-yl)pyridine, 3',5'-di(carbazol-9-yl)-[1,1'-biphenyl]-3,5-dicarbonitrile, 4,4'-(9H,9'H-3,3'-bicarbazole-9,9'-diyl)bis(N,N-diphenylaniline), 4'-(9H-carbazol-9-yl)biphenyl-3,5-dicarbonitrile, 3'-(9H-carbazol-9-yl)biphenyl-3,5-dicarbonitrile, 2,8-bis(diphenylphosphoryl)dibenzo[b,d]furan, and 3,5-di(carbazol-9-yl)-1-phenylsulfonylbenzene. The compound of Formula 1 can be present in the host material at a concentration of 1-20% w/w.

The light-emitting material can be deposited using any suitable conventional method known in the art including, but not limited to, vacuum deposition, spin coating, printing, print screening, spraying, painting, doctor-blading, slot-die coating, and dip coating.

Any suitable electron-transport material may be used to form the electron-transport layer 150. As the electron-transport material, any electron-transporting material that can stably transport electrons injected from an electron injecting electrode (cathode) may be used as a material for the electron-transport layer. Non-limiting examples of useful electron-transport materials may include quinoline derivatives such as tris(8-quinolinorate)aluminum (Alq3), 3-(biphenyl-4-yl)-4-phenyl-5-(4-t-butylphenyl)-1,2,4-triazole (TAZ), bis(2-methyl-8-quinolinato-N1,O8)-(1,1'-biphenyl-4-olato)aluminum (BAlq), beryllium bis(benzoquinolin-10-olate) (Bebg2), 9,10-di(naphthalene-2-yl)anthracene (ADN), 1,3,5-Tris(3-pyridyl-3-phenyl)benzene (TmPyPB), and (3,3",5,5"-tetra(pyridin-3-yl)-1,1': 3',1"-terphenyl (BmPyPhB).

The electron-transport material can be deposited using any suitable conventional method known in the art including, but not limited to, vacuum deposition, spin coating, printing, print screening, spraying, painting, doctor-blading, slot-die coating, and dip coating.

Any suitable electron-injection material may be used to form the electron-injection layer 160. Non-limiting examples of electron injecting materials useful for forming the electron-injection layer 160 are LiF, NaCl, CsF, $Li_2O$, 8-hydroxyquinolinolato-lithium (Liq) and BaO.

The electron-injection material can be deposited using any suitable conventional method known in the art including, but not limited to, vacuum deposition, spin coating, printing, print screening, spraying, painting, doctor-blading, slot-die coating, and dip coating.

The cathode 170 can comprise any anodic material known to those of skill in the art. In certain embodiments, the anode comprises lithium, magnesium, calcium, aluminum, gold, indium, copper, silver, or a combination thereof. In certain embodiments, the anode comprises aluminum.

The cathode 170 can be deposited using any suitable way such as evaporation, sputtering, chemical vapor deposition, or electrochemical processes. Anodes can be patterned using, e.g., conventional photolithographic processes.

In certain embodiments, the OLED comprises thin layers of ITO/HATCN/TAPC/AIEgen 1/TmPyPB/LiF/Al, wherein HATCN and LiF serve as the hole-injection and electron-injection layers, respectively; TAPC and TmPyPB serve as the hole-transport and electron-transport layers, respectively; AIEgen 1 serves as the light-emitting layer; and ITO and Al are used as the anode and electrode, respectively.

The luminescent devices described herein can be incorporated into a wide variety of consumer products, including flat panel displays, computer monitors, televisions, billboards, lights for interior or exterior illumination and/or signaling, sensors, heads up displays, fully transparent displays, flexible displays, cell phones, personal laptop computers, digital cameras, camcorders, viewfinders, microdisplays, vehicles, a large area wall, theater or stadium screen, or a sign.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures described herein.

Figure 5:
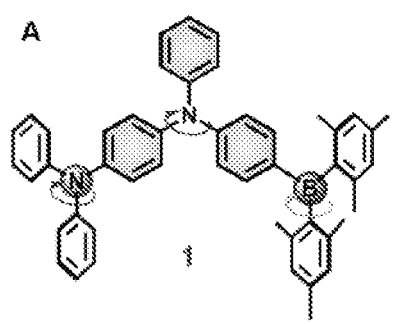
FIG. 5 depicts (A) The molecular structure of AIEgen 1. (B) PL spectra of AIEgen 1 ($1.0 \times 10^{-5}$ M) in DMF-water mixtures, $\lambda_{ex}$=390 nm. (C) Plot of relative maximum emission peak intensity ($\alpha_{AIE}$) at 500 nm versus $f_w$ of the DMF/water mixture, where $\alpha_{AIE}$=I/I$_0$, I=emission intensity and I$_0$=emission intensity in DMF solution. Inset: photos taken under 365 nm UV light of AIEgen 1 in DMF-water mixtures.
Figure 5:
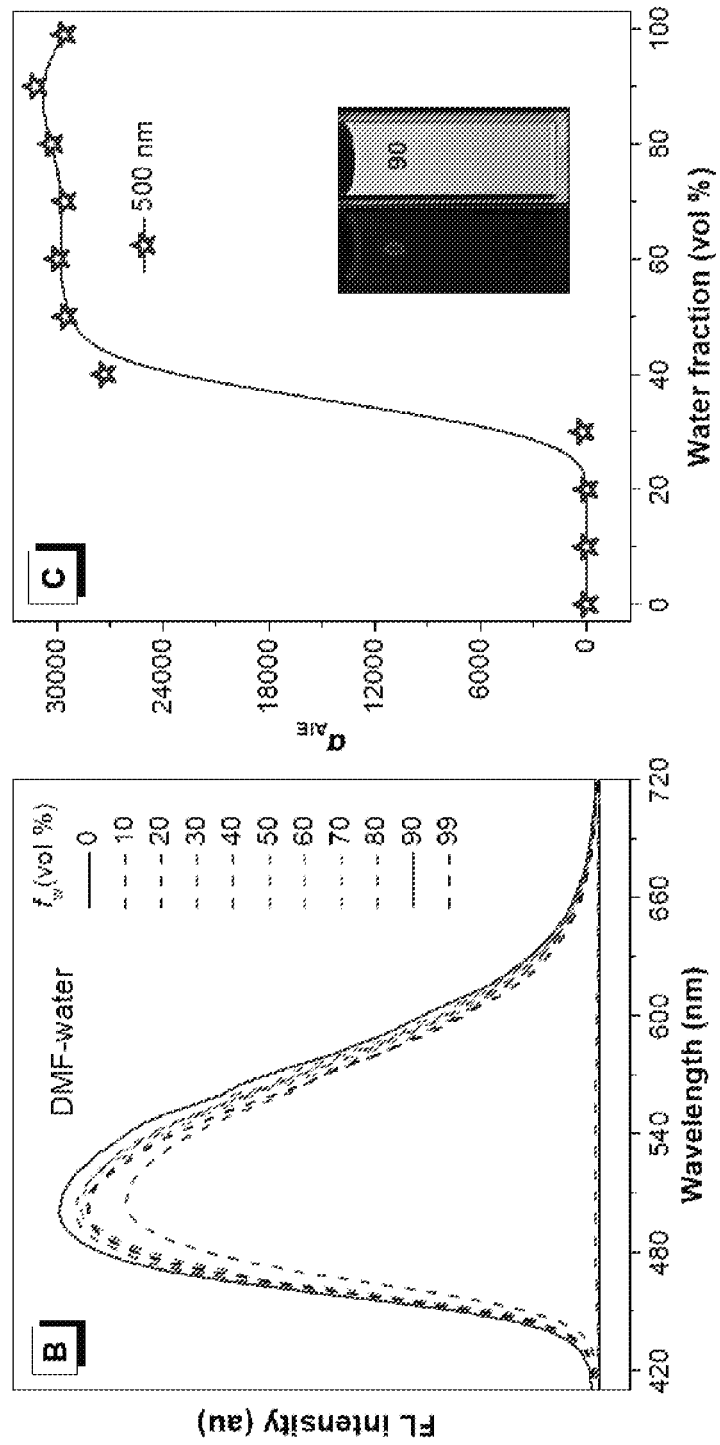

AIEgen 1 featuring a propeller shaped structure exhibits AIE properties (FIG. 5). When the sample of AIEgen 1 was dissolved in pure DMF solvent at low concentration, the solution was completely non-emissive. However, with the addition of water, its emission increased with a dramatic ~27,000-fold enhancement when the water fraction reached 40%, while the luminescence intensity remained almost unchanged with further increase of water fractions. The single crystal structure of AIEgen 1 bears a very twisted molecular conformation with the corresponding torsion angles of 31.23 ($\theta_1$), 39.34 ($\theta_2$), 39.32 ($\theta_3$), 57.85 ($\theta_4$), and 47.72 ($\theta_5$), respectively. Accordingly, the rotations of multiple flexible aryl rotors are greatly restricted in different aggregate states, which is believed to block the radiationless consumption of the excitation energy and facilitates the radiative decay channel, and thus AIEgen 1 and the compounds described herein can become highly emissive.

Figure 6:
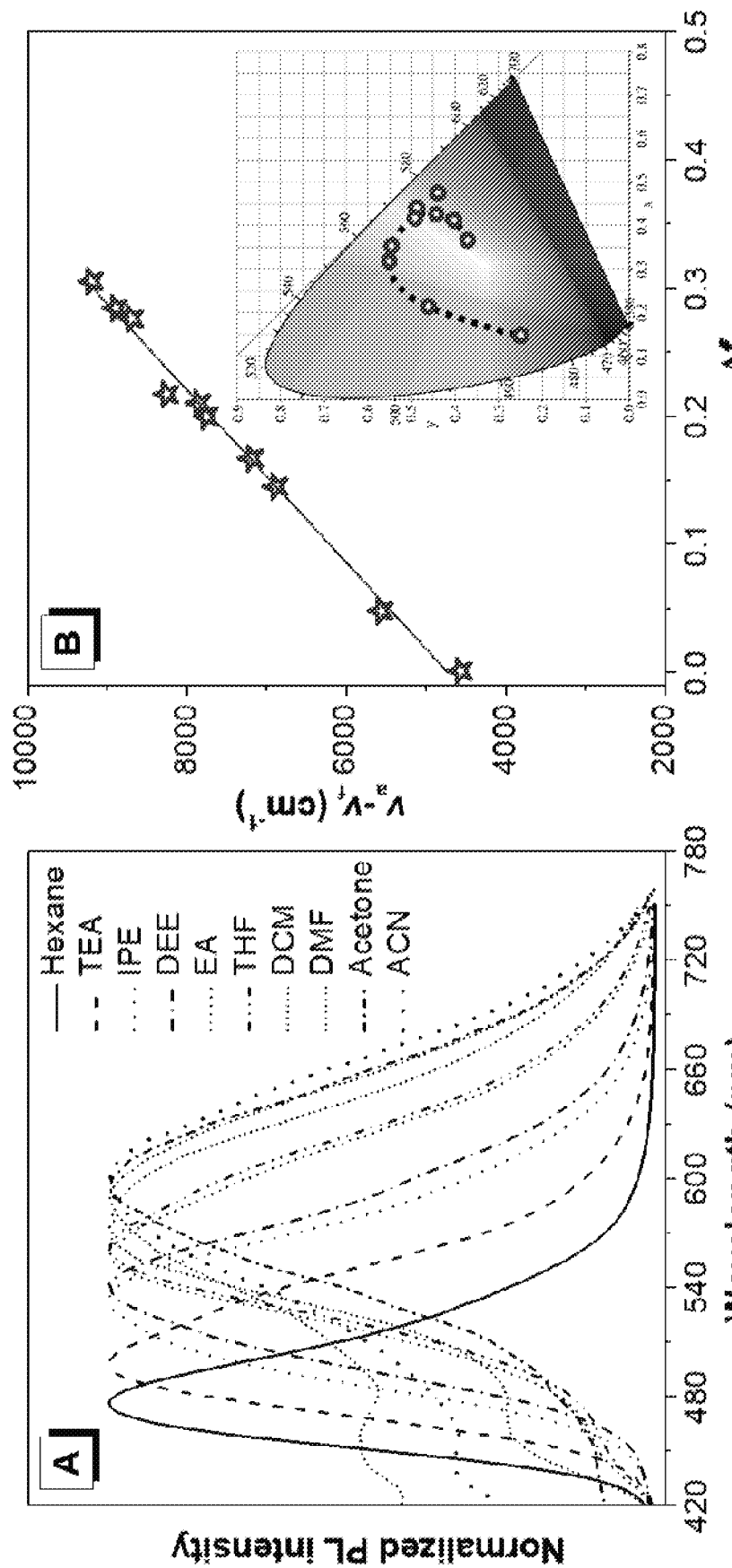
FIG. 6 depicts the (A) PL spectra of AIEgen 1 measured in different solvents. (B) Linear correlation of the orientation polarization ($\Delta f$) of solvent with Stokes shift ($v_a$-$v_f$) for AIEgen 1 ($R^2$=0.991). Inset: CIE chromaticity diagram showing the temperature dependence of the (x, y) color coordinates of AIEgen 1. Concentration: $1.0 \times 10^{-5}$ M; $\lambda_{ex}$=390 nm. Abbreviation: TEA=triethylamine, IPE=isopropyl ether, DEE=diethyl ether, EA=ethyl acetate, THF=tetrahydrofuran, DCM=dichloromethane, DMF=N,N'-dimethylformamide, ACN=acetonitrile.

A large molecular dipole of D-A structures can yield intriguing photoluminescence behavior depending on the solvent polarity due to the conversion between less polarized locally excited (LE) state and polarized twisted intramolecular charge transfer (TICT) state. AIEgen 1 demonstrated a strong solvatochromic effect. When the solvent polarity was increased gradually from low-polarity hexane to high-polarity acetonitrile, the emission of its solution exhibited a dramatic bathochromic shift and the intensity gradually weakened due to the susceptibility of the TICT state to various nonradiative quenching processes. Meanwhile, its solution colors changed from bright blue in nonpolar hexane over green, yellow and orange in lower polar solvents (such as ether, ethyl acetate, THF and DCM) and then to dark red in high polar solvents (acetone, DMF and acetonitrile), thus covering the whole visible region as shown in the CIE diagram obtained from the PL spectra (FIG. 6B), and allowing even a visual estimate of the solvent polarity. In sharp contrast, its absorption spectra displayed no obvious change as the solvent polarity increased. Quantitatively, the relationship between the Stokes shift ($v_a-v_f$) of the luminogen and solvent parameters, or the orientation polarizability f ($\varepsilon$, n) can be described by the Lippert-Mataga equation:

$$hc(v_a - v_f) = hc(v_a^0 - v_f^0) + \frac{2(\mu_e - \mu_g)^2}{a^3} f(\varepsilon, n)$$

where h is Plank's constant, c is the velocity of light, f is the orientational polarizability of the solvent, $v_a^0-v_f^0$ corresponds to the Stokes shifts when f is zero, $\mu_e$ is the excited-state dipole moment, $\mu_g$ is the ground-state dipole moment, $\alpha$ is the solvent Onsager cavity radius, and $\varepsilon$ and n are the solvent dielectric and the solvent refractive index, respectively (Table 2, FIG. 18). As shown in FIG. 6B, the experimental data of AIEgen 1 obeys a good linear relationship expected by Lippert-Mataga equation in the whole range of solvent polarity, further confirming its typical TICT character. Additionally, obvious charge separation in its natural transition orbitals (NTO) of the first singlet excited state also verified the large molecular dipole of AIEgen 1 further reflecting its ICT character (FIG. 7). The aforesaid solvatochromic PL behavior is essentially a visualization for marked solvent polarity changes which takes place on a molecular-microscopic level. It is more appealing that the compounds described herein could also achieve the visualization of subtle polarity changes, details see below.

Figure 9:
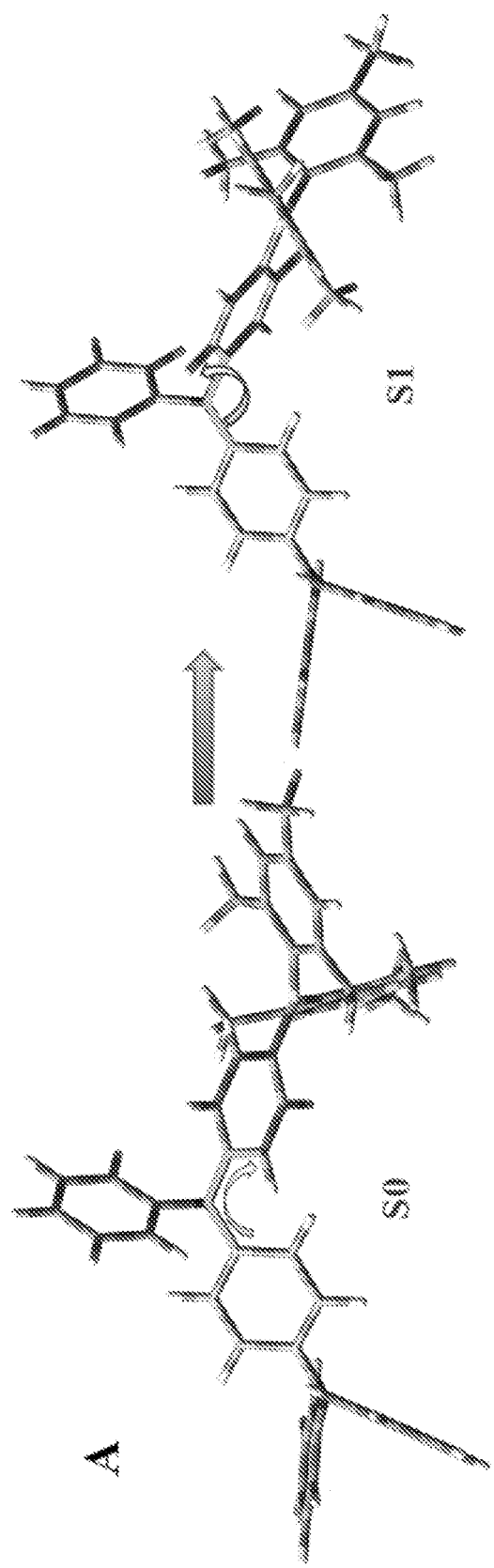
FIG. 9 depicts the (A) temperature-dependent fluorescence spectra of AIEgen 1 in THF solution ($1 \times 10^{-5}$ M; $\lambda_{ex}$=390 nm). (B) Plot of the corresponding intensity ratio ($\lambda_{556}/\lambda_{596}$) with temperature ($R^2$=0.988).
Figure 10:
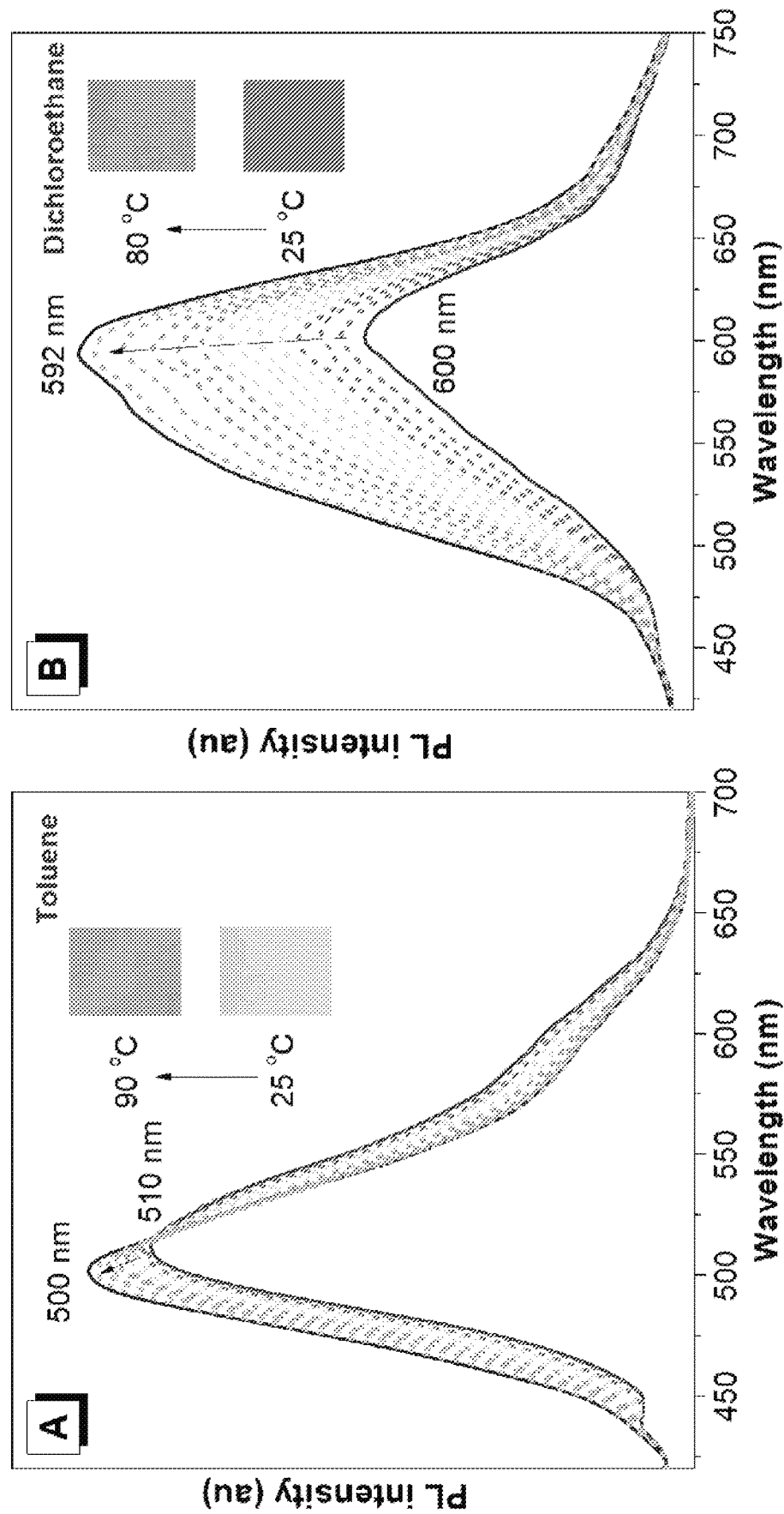
FIG. 10 depicts the temperature-dependent fluorescence spectra of compound AIEgen 1 in different solvents: (A) toluene, (B) dichloroethane, and (C) o-dichlorobenzene ($1 \times 10^{-5}$ M, $\lambda_{ex}$=390 nm). Inset: Photographs of fluorescence at different temperatures.
Figure 10:
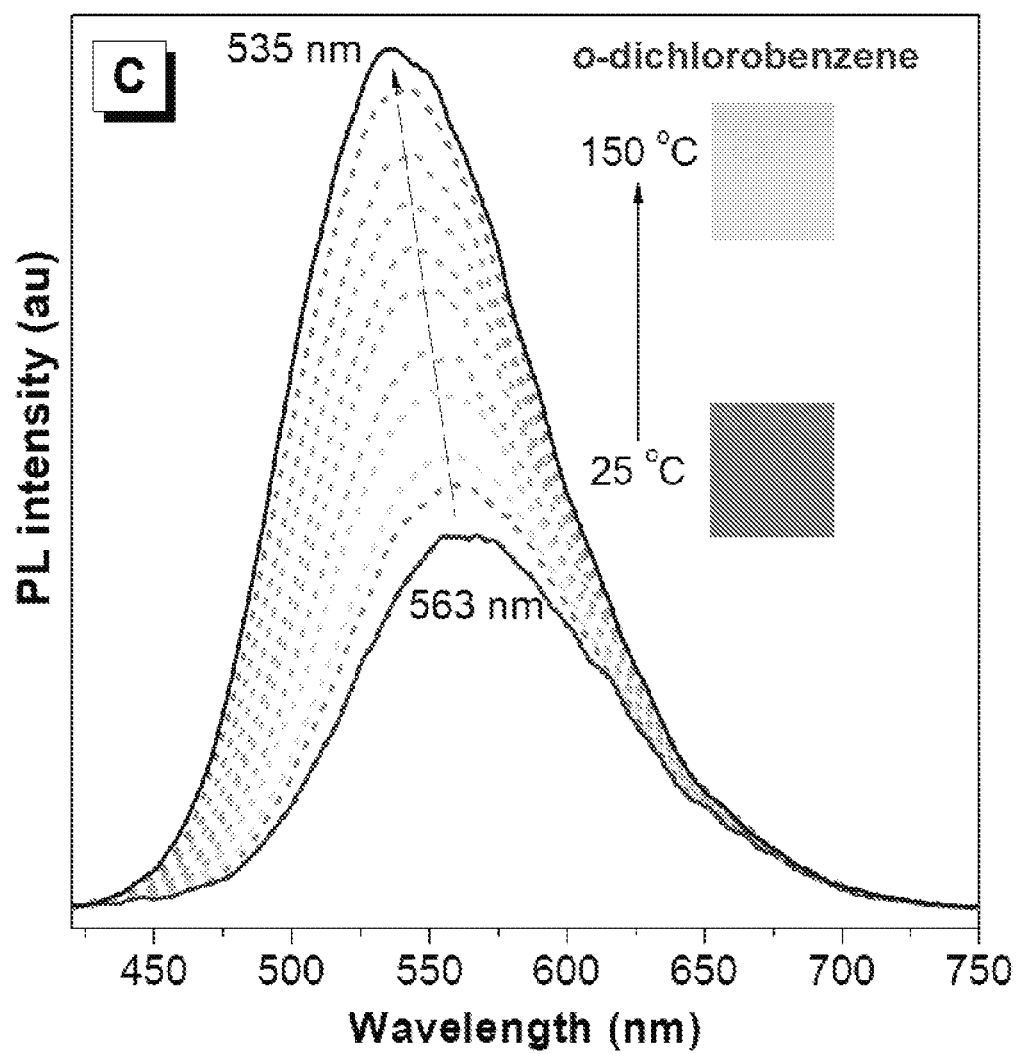

In general, the luminescence of organic compounds in solution state is quenched with the increase of temperature. However, it is intriguing that the compounds described herein can achieve a continuously enhanced emission by increasing temperature. From another perspective, this temperature effect is also powerful evidence to reinforce that the TICT process is really involved. Typically, in THF solvent with a moderate polarity, two discernable bands centered at 556 and 596 nm related to the LE state and the TICT state, respectively, could be observed. As demonstrated in FIG. 9, increasing the temperature from 29° C. to 47° C. led to a change of their relative intensities. Additionally, there is an excellent linearity between their intensity ratio ($\lambda_{556}/\lambda_{596}$) and the temperature in the range from 29° C. to 47° C., including a vital physiological temperature range, suggesting that the present ratiometric system may be useful for the quantitative determination of temperature. More interestingly, a noticeable luminescence color transition from dark orange to bright yellow was accompanied with the above temperature elevation process. Therefore, the compounds described herein can realize colorimetric and ratiometric temperature detection. It has been recognized that solvent polarity is heavily temperature-dependent. In weakly polar toluene, similar intensity-intensified and blue-shifted tendency could be observed with the increase of temperature, while these variations were comparatively more conspicuous and were accompanied by striking color changes in relatively higher polarized solvents, i.e. dichloroethane and o-dichlorobenzene, as shown in FIG. 10.

Figure 11:
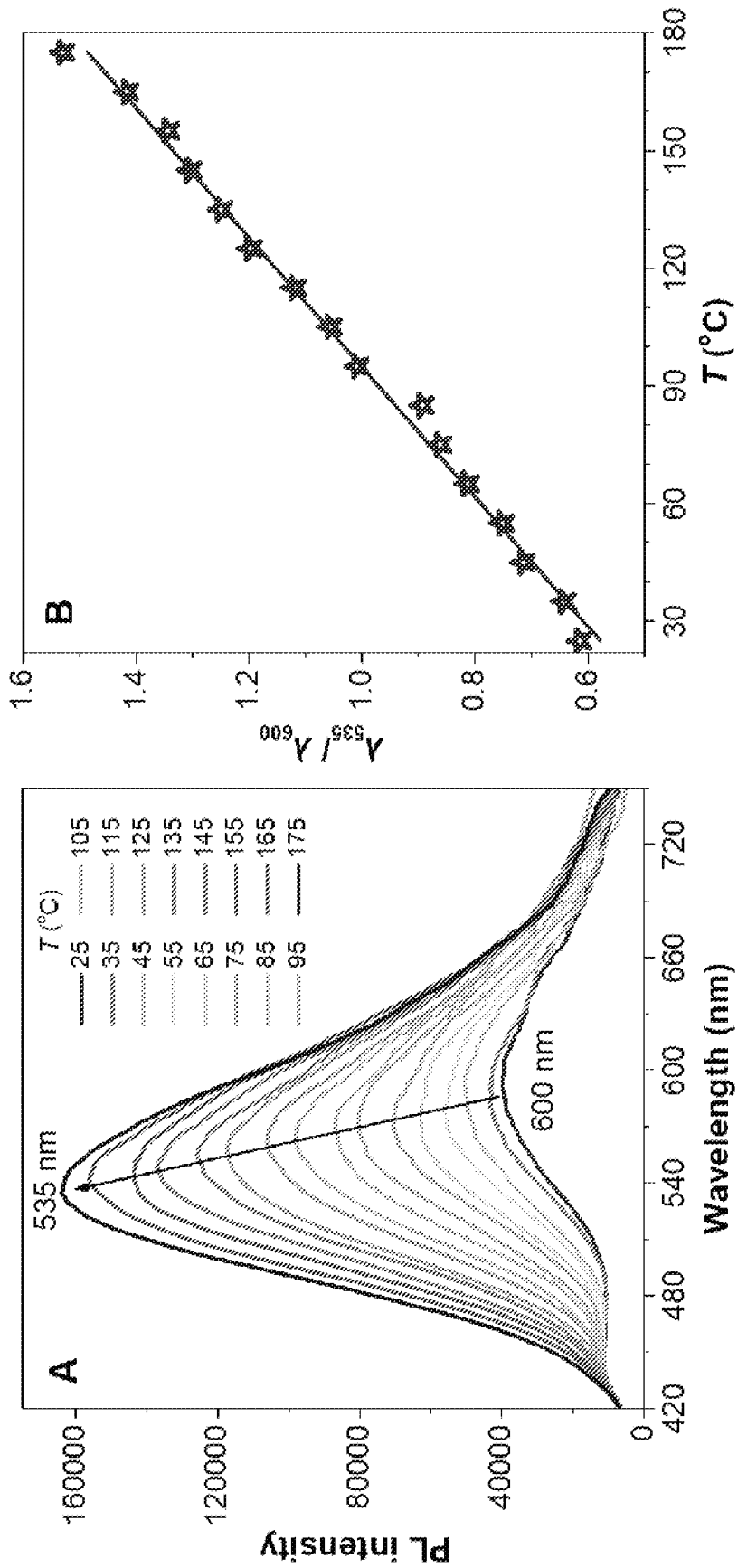
FIG. 11 depicts the (A) temperature-dependent fluorescence spectra and (B) plot of the corresponding intensity ratio ($\lambda_{535}/\lambda_{600}$) of AIEgen 1 in tetraethylene glycol dimethyl ether with temperature ($1 \times 10^{-5}$ M, $\lambda_{ex}$=390 nm, $R^2$=0.993). (C) CIE chromaticity diagram showing the temperature dependence of the (x, y) color coordinates of AIEgen 1. (D) The gradient fluorescence of AIEgen 1 solution in a quartz tube.
Figure 11:
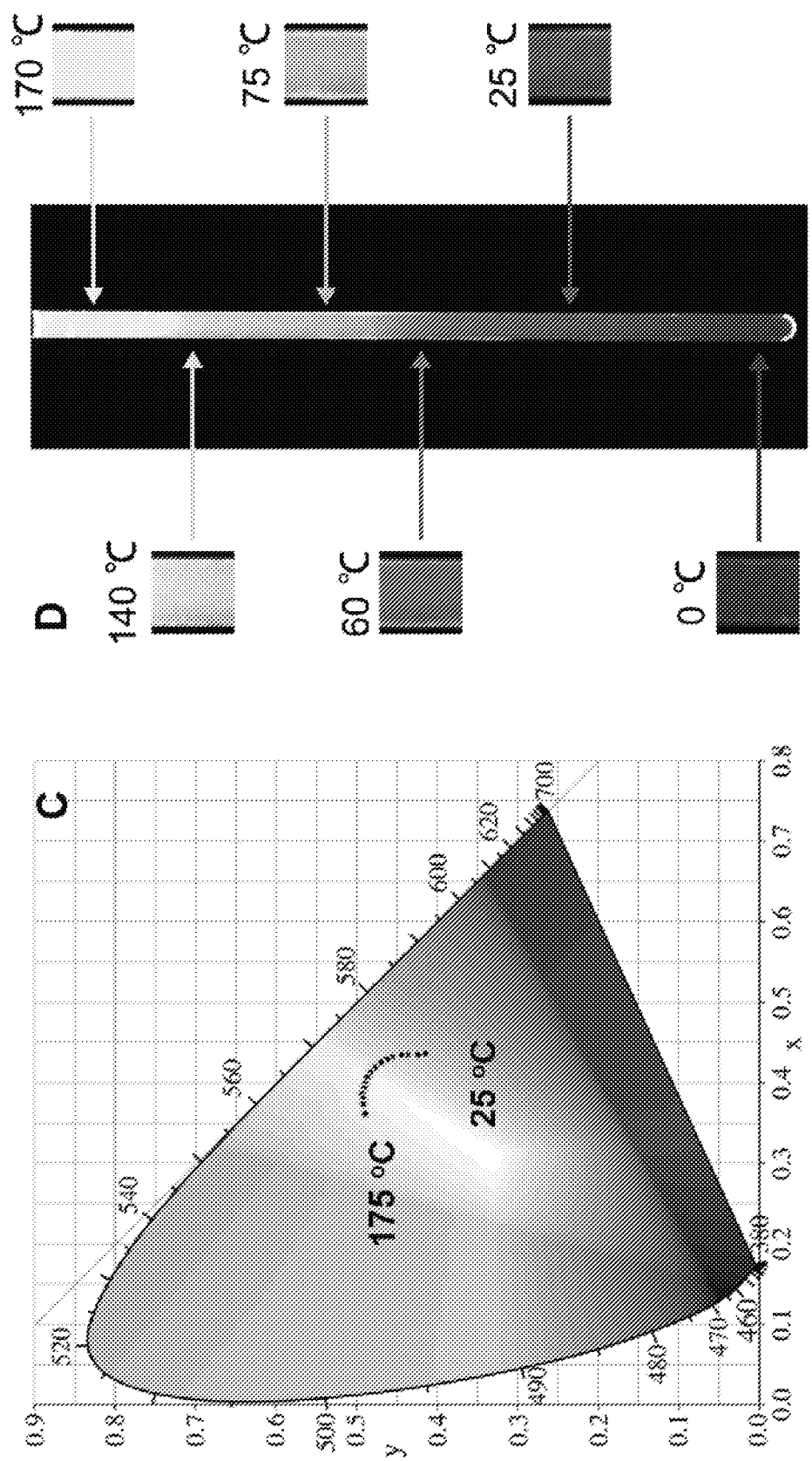

Herein, it is noteworthy to mention that polarity is an important parameter in chemistry, nanotechnology, and even life science. In biological systems, especially at the cellular level, polarity determines the interaction activity of large numbers of proteins and enzymes or reflects the permeability of membrane compartments. Furthermore, abnormal changes in polarity are closely linked with disorders and diseases (e.g., diabetes, liver cirrhosis). However, the environmental polarity change in many cases is relatively subtle, especially for the above biological systems and the aforementioned temperature-dependent systems, thus it is very difficult to realize its accurate measurement in a straightforward manner, let alone its macroscopic visualization. Therefore, the compounds described herein, involving simple ratiometric measurement of fluorescence signals, readily realized a dramatic amplification of the subtle polarity change as a function of temperature. Additionally, this microcosmic change has been well presented by macroscopic color changes of the system. Therefore, the present signal amplification and visualization method provides a valuable tool for the measurement of subtle polarity change. In another aspect, thermochromic solutions of the compounds described herein, such as AIEgen 1, also allow a simple quantitative determination of the temperature dependence, thus possessing great potential to be used as luminescent thermometer. In order to test its response range and facilitate its application, we have selected tetraethylene glycol dimethyl ether (TRIEDM) with a very high boiling point of 275° C. and ideal stability as the solvent. As shown in FIG. 11, the emission band of AIEgen 1 gradually blue shifted and the corresponding intensity was continuously enhanced with the increase of temperature. Advantageously, the luminescence color also exhibited obvious conversion from orange to bright yellow-green. It is reasonable to predict that the above change tendency would be continuous if temperature condition permits and its solution colors likely cover the whole visible region as shown in the CIE diagram in FIG. 11C. Moreover, there is also a good linear relationship between the intensity ratio ($\lambda_{535}/\lambda_{600}$) and the temperature in a wide range of 25 to 175° C. It should be mentioned that the above temperature-dependent emission evolution and color conversion are completely reversible. Such intriguing properties inspired us to fabricate a simple liquid thermometer by utilizing the above TRIEDM solution system. As illustrated in FIG. 11D, when we heated the above solution from the top and synchronously cooled it from the bottom, apparent color changed pattern, corresponding to specific temperature gradient, could be directly observed with our naked eyes. This is only a very simple trial but it is reasonable to anticipate that the above color switching should be much more prominent if higher temperature can be achieved. In light of the excellent properties, our system should be a promising candidate for high performance thermometers with a wide detection range and high upper limit.

Thus, provided herein is a method for measuring the temperature, the method comprising measuring the fluorescence emission of a sample comprising a compound described herein; and determining the temperature based on the measured fluorescence emission. The step of determining the temperature based on the measured fluorescence can comprise comparing the measured fluorescence to fluorescence of a standardized curve or comparing to the measured fluorescence to a color chart. The measured temperature can be any temperature. In certain embodiments, the measured temperature is in the range of −100 to 350° C. In certain embodiments, the measured temperature in the range of −50 to 300° C., 0 to 300° C., 0 to 250° C., 0 to 200° C., 10 to 200° C., 20 to 200° C., 20 to 180° C., 25 to 175° C. or higher.

Also provided is a device for measuring the temperature comprising the compound described herein and a solvent. In certain embodiments, the solvent is an organic solvent. The selection of the organic solvent and its respective boiling point can be selected based on the desired temperature monitoring range. In certain embodiments, the boiling point of the solvent is 50 to 500° C., 100 to 400° C., 100 to 300° C., 100 to 300° C., 150 to 300° C., or 200 to 300° C. In certain embodiments, the solvent is TRIEDM.

Figure 12:
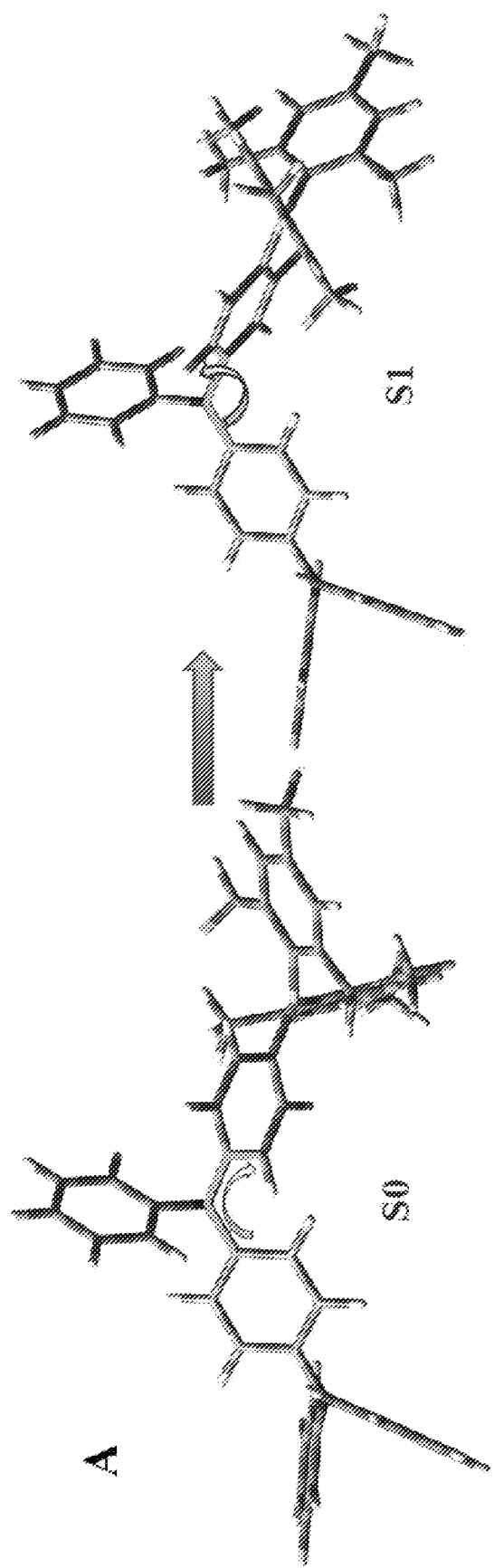
FIG. 12 depicts the (A) Molecular structures of the ground state and the excited state of AIEgen 1 based on TDDFT calculations at B3LYP/6-31G(d) level. (B) Simulated fluorescence spectra and (C) calculated potential energies of different conformations in the excited state of AIEgen 1.
Figure 12:
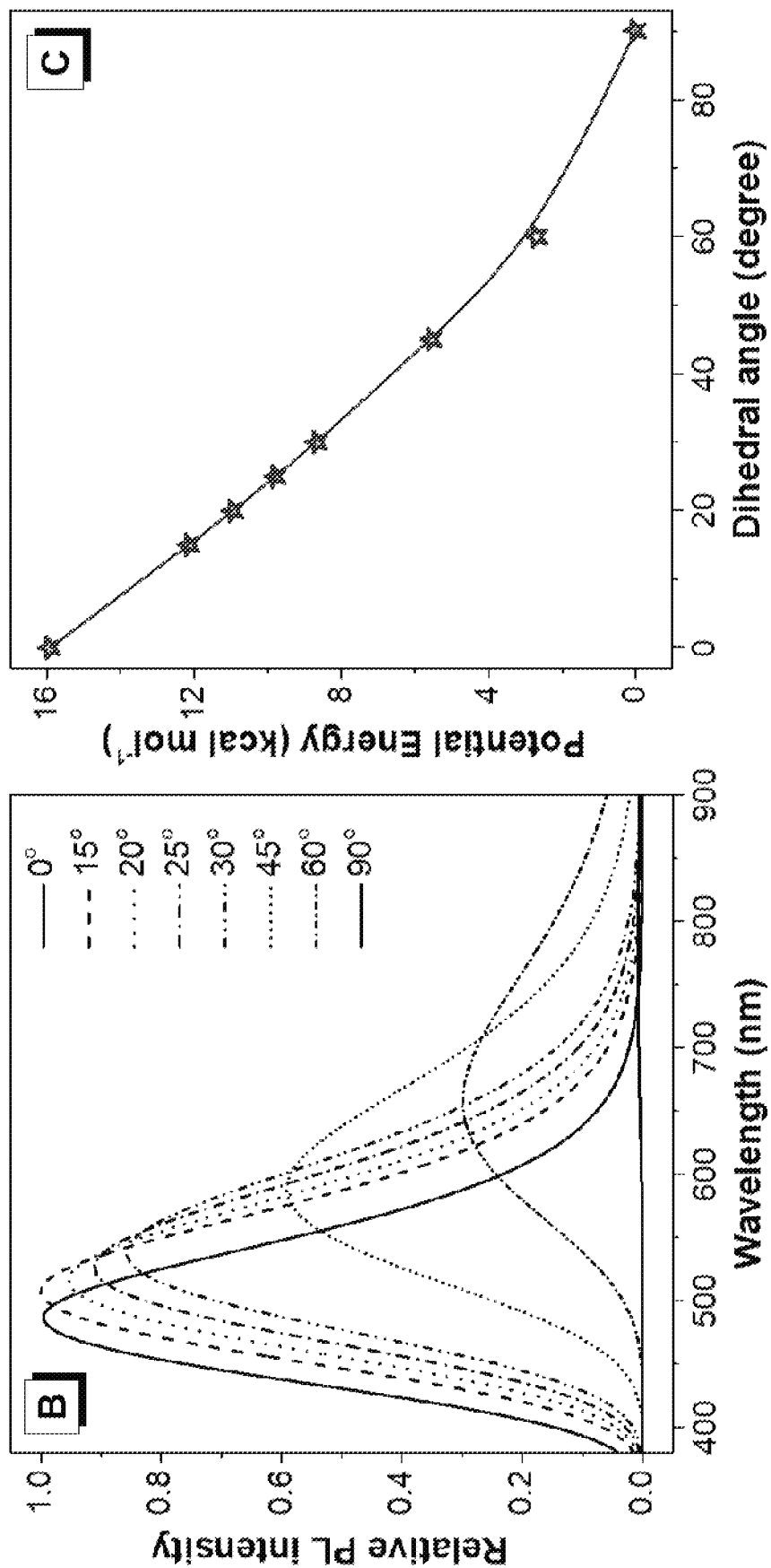

The underlying mechanism of the thermochromic PL of the compounds described herein was then investigated, with the goal of providing an initial guideline for the design of new thermochromic materials. Taking all the experimental data together, we proposed that raising temperature will lead to the increase of solvent hydrophobicity, thus benefiting the LE state prone to planar geometry and resulting in intensified emission intensities and blue-shifted luminescence. Given that temperature switching is considered to induce dynamic changes in molecular structures. Considering there are multiple flexible aryl rotors in the compounds described herein, various conformations of the excited state S1 were attempted. Ultimately, it was observed that the central plane formed by atoms C16, N2 and C25 is the pivot to determine the flexible conformation, and is also the critical position linking the charge separated donor and acceptor units. Upon excitation to S1, the molecule rotates around the N2-C25 bond, and the associated C16-N2-C25-C30 dihedral angle varies from ~30° to ~90°, thus possessing a more twisted conformation as demonstrated in FIG. 12A. Combined with the most populated transitions of molecular orbitals, the twisting degree of molecular conformations could be well elucidated by the variation of central dihedral angle C16-N2-C25-C30. In order to clarify its influence on the photoluminescence, the PL spectra of eight different conformations was calculated by scanning different twisting angles of C16-N2-C25-C30. As shown in FIG. 12C, a gradual red shift and attenuation of photoluminescence could be observed with the dihedral angle varying from 0° to 90°. These results revealed that more planar conformation should greatly facilitate the fluorescence emission. The potential energies of these eight conformations in the excited states was calculated. The potential energy of the planar conformation with 0° is about 14 kcal/mol higher than that of the twisted conformation with 90°, thereby further indicating much higher stability of the latter. The theoretical calculations together with the evidences from the thermochromic study reinforced our previous envision that the temperature strongly influenced the dynamic equilibrium between the LE and TICT excited states and higher temperature is suggested to facilitate the stability of planar geometry with LE character, further resulting in blue-shifted and enhanced photoluminescence.

Figure 13:
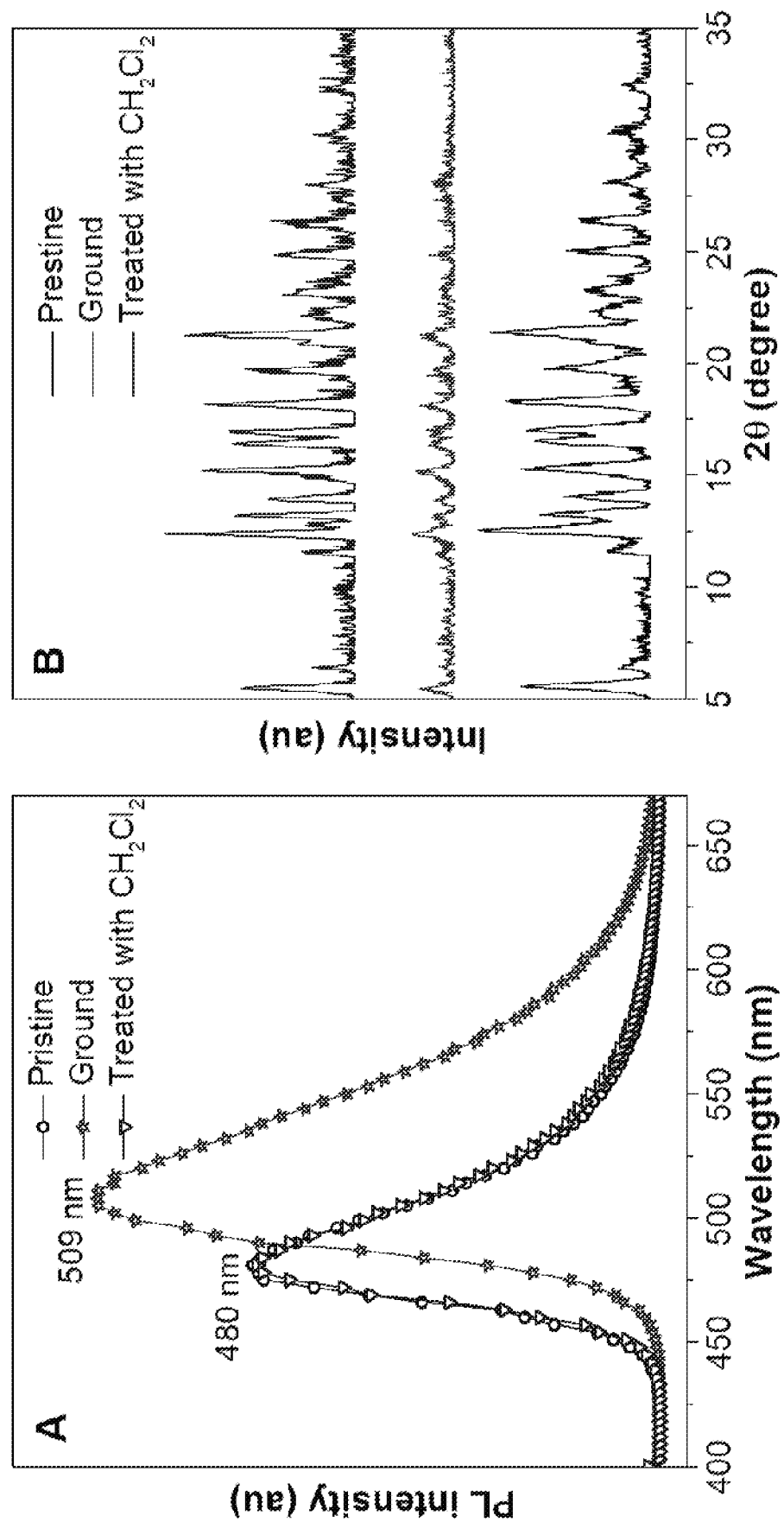
FIG. 13 depicts the (A) PL spectra of AIEgen 1 before grinding, after grinding, and after treatment with dichloromethane vapor. $\lambda_{ex}$=390 nm. (B) PXRD patterns of AIEgen 1 at different states and (C) photographs taken under irradiation with 365 nm UV light. (D) Writing and erasing of letters "AIE" on the filter paper using AIEgen 1 taken under UV light.
Figure 13:
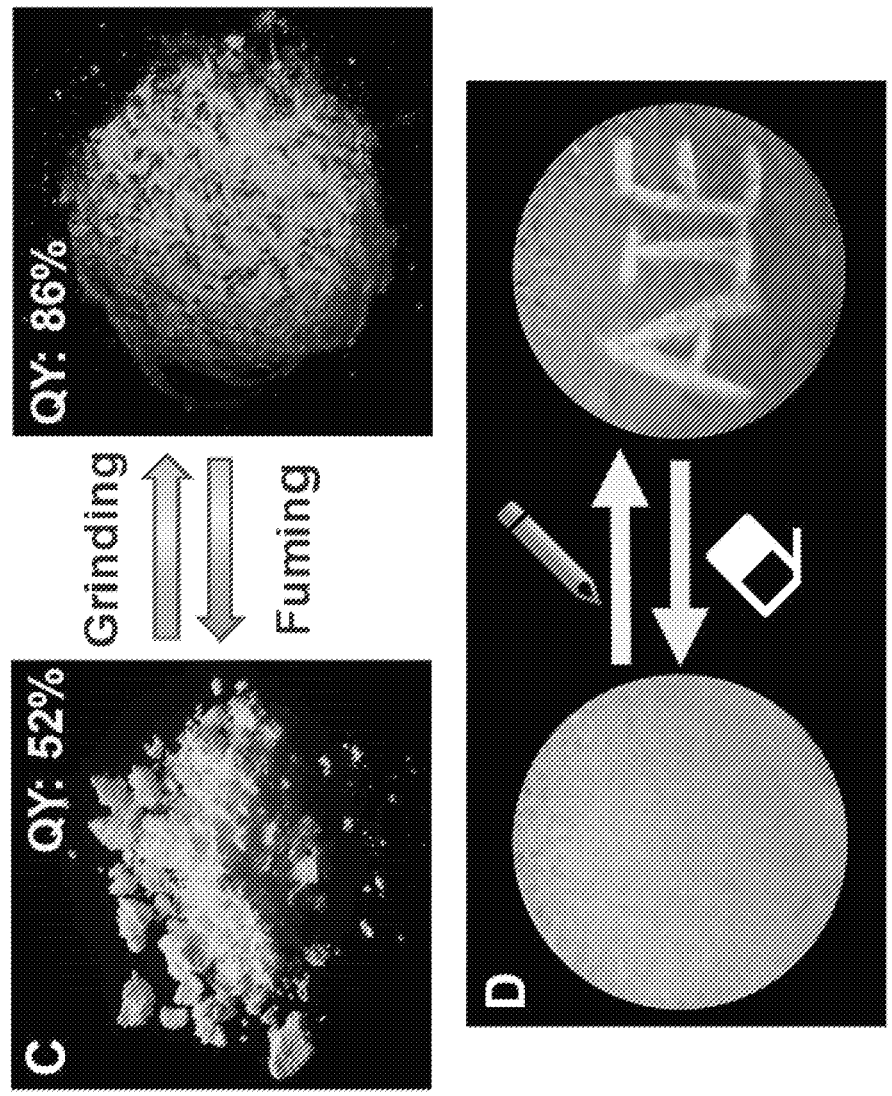
Figure 14:
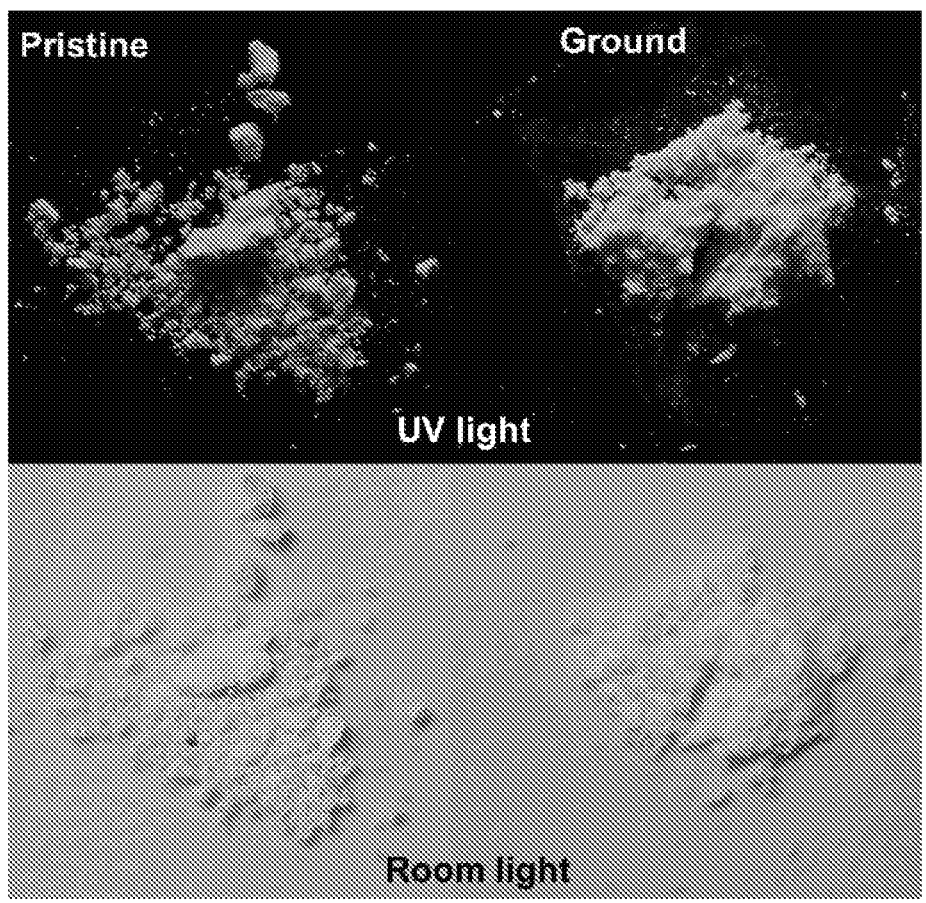
FIG. 14 depicts photos of pristine (left) and ground (right) samples of AIEgen 1 taken under room and UV light irradiation.

Excitingly, this compound is very sensitive to the external shear force stimulus and exhibits attractive tribochromic PL behavior (FIG. 13). We found that the solid showed red-shifted and remarkably enhanced emission when the powder was ground under shearing force. Upon grinding, its emission color changed from blue to yellow-green with the maximal fluorescent peak shifted from 480 nm to 509 nm, and the corresponding quantum yield also dramatically increased up to 86% from the original 52% (FIGS. 13A and 13C). Surprisingly, the color transition after grinding could be directly observed with naked eyes in daylight (FIG. 14). When the ground powder was exposed to dichloromethane (DCM) vapor, the original blue state could be restored completely as the PL spectra verified, indicative of a reversible tribo-responsive process. Given its excellent triochromic PL behavior, the practical application in rewritable paper was explored. By immersing the filter paper into the DCM solution of AIEgen 1 and then drying by blower, a blue emissive rewritable paper was prepared, on which legible yellow-green letters such as "AIE" with a sharp rod could be inscribed. When exposing the filter paper in DCM atmosphere for a few minutes, the written letters can be easily erased. And the above writing-erasing process could be repeated many times. Accordingly, the compounds described herein could potentially be applicable for security inks and papers. Thus, provided herein is rewritable paper system comprising paper and a compound described herein. Also provided in a security ink comprising a compound described herein.

Powder X-ray diffraction (pXRD) measurement was performed on an AIEgen 1 sample in different states to examine the tribochromic PL mechanism. As demonstrated in FIG. 13B, the pristine state of AIEgen 1 exhibits sharp and intense diffraction peaks, suggesting a well-defined crystalline state; while relatively weak reflections could be observed after grinding, indicative of significant destruction of crystalline state by mechanical forces. In this state, the amorphous species should be predominantly produced. Upon fuming in the DCM atmosphere, the original sharp signals could be restored, which reveals the recovery of the crystalline state. Therefore, the observed tribochromic PL behavior of AIEgen 1 is explicitly involved in a reversible morphological transformation between the blue crystalline state and the amorphous yellow-green state.

Figure 15:
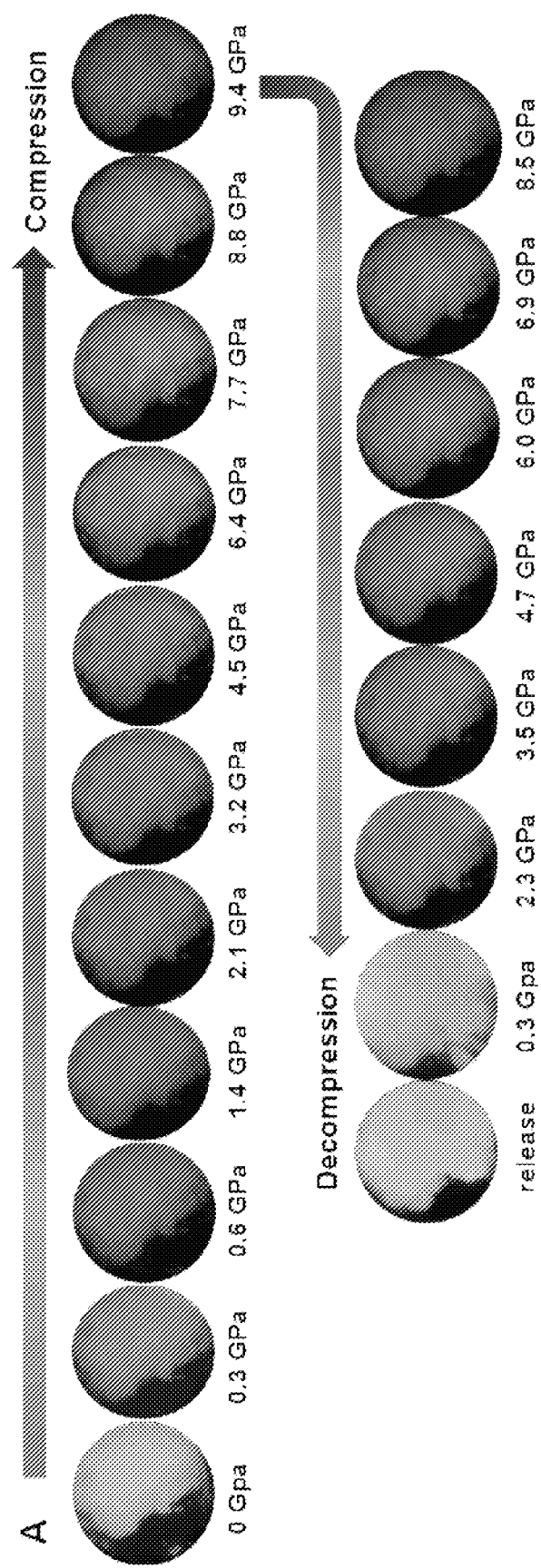
FIG. 15 depicts (A) photos of AIEgen 1 powder taken under different pressure. Fluorescent spectra of AIEgen 1 powder during (B) compression and (C) decompression, via a diamond anvil cell (DAC). (D) Raman spectra of AIEgen 1 powder taken at different pressures. Excitation wavelength was 365 nm.
Figure 15:
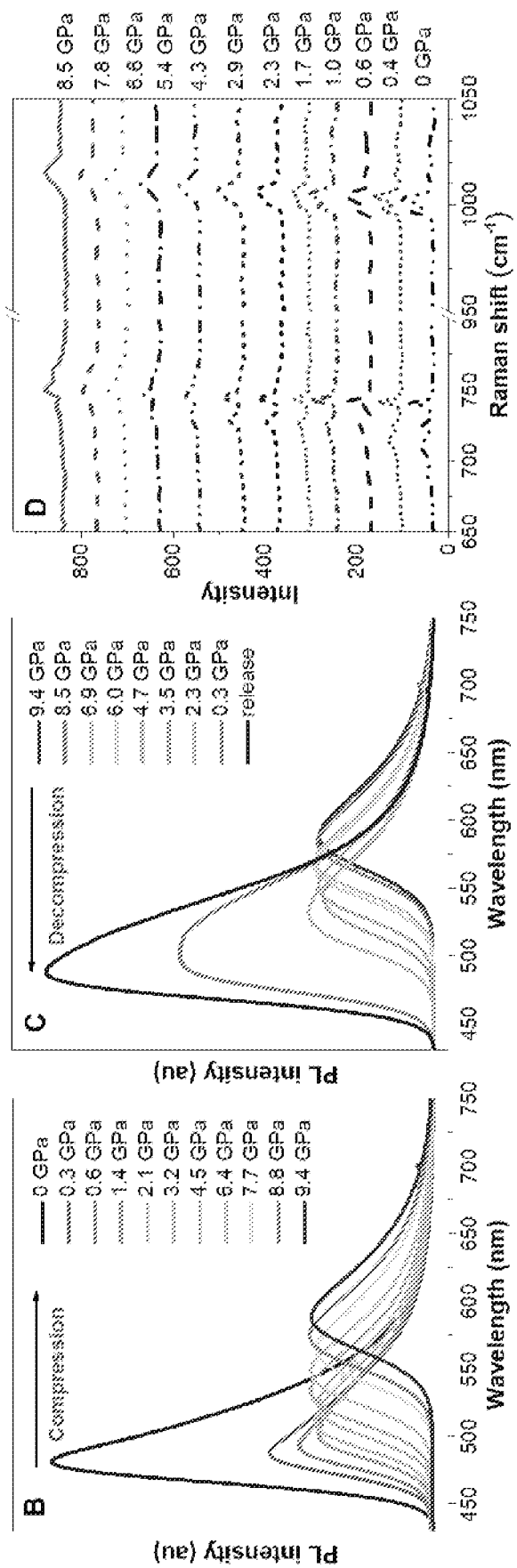
Figure 16:
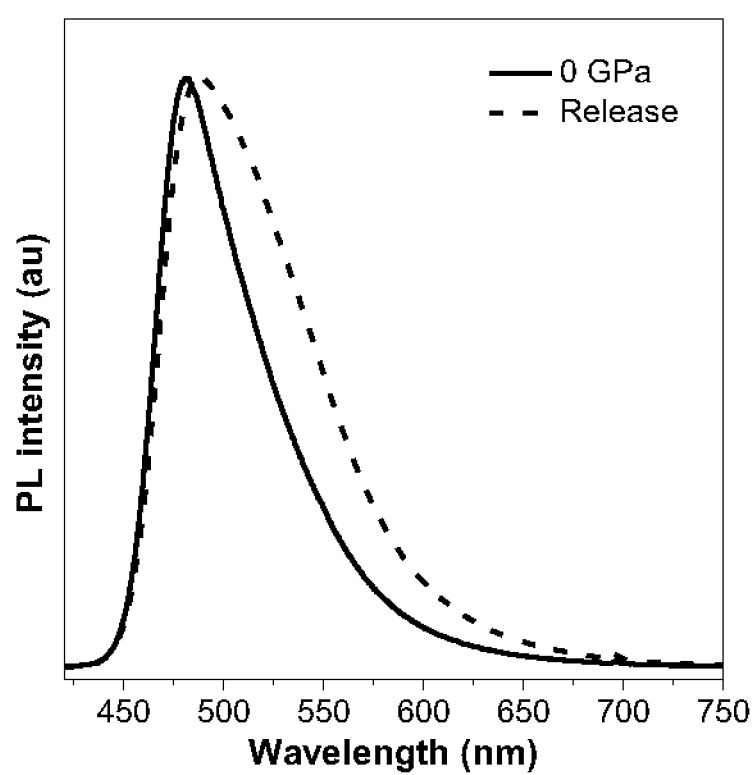
FIG. 16 depicts the recovery properties of AIEgen 1 powder via DAC. Excitation wavelength was 365 nm.

Given that the compounds described herein can respond to anisotropic shearing force, the compound's responsive behavior to isotropic hydrostatic pressure was examined. As shown in FIG. 15, AIEgen 1 suffered remarkable and continuous color variation over three stages from blue to yellow and then to orange with increasing in situ pressure. Concomitantly, the fluorescence spectra exhibited a gradual red shift from 481 nm to 588 nm (FIG. 15B), but its intensity decreased continuously, which is noticeably different from that of its ground state. However, once the pressure was released, it gradually reverted back to the initial state (FIG. 15C and FIG. 16). To probe the structural change during the above piezochromic PL process, an in situ high-pressure Raman experiment was performed on AIEgen 1. As demonstrated in FIG. 15D and FIG. 17, all the Raman peaks displayed blue-shift with elevated external pressure, which is presumably attributed to the simultaneously shortened bond lengths and decreased intermolecular distances.

Figures 20, 21:
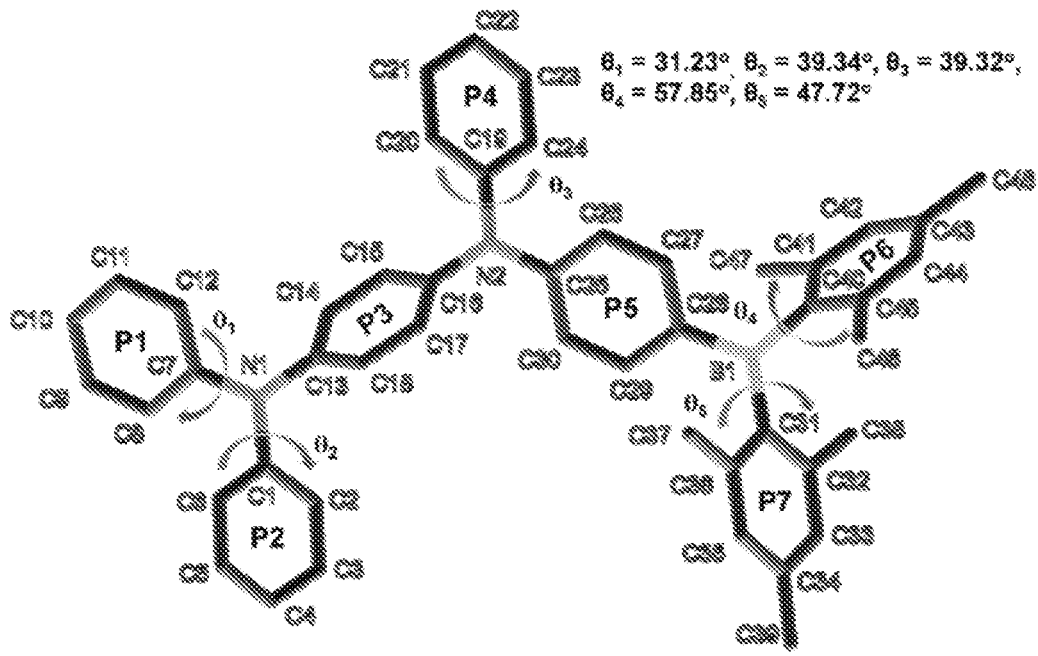
FIG. 20 depicts the crystal structure of AIEgen 1(P1-P7: labels of phenyl rings).
FIG. 21 depicts Table 3 That shows experimental and DFT calculation simulated (B3LYP/6-31G(d)) Raman internal modes of AIEgen 1. Crystallographic data for the structures reported in this work have been deposited with the Cambridge Crystallographic Data Centre as supplementary publication no. CCDC: 1884262.

Combined with the DFT calculation results (Table 3, FIG. 21), the peaks at 709, 723, and 740 $cm^{-1}$ are attributed to the C—H bond off-plane wagging vibrations, and their respective intensities gradually decreased with the increase of pressure; while the peaks ascribed to breathing vibrations of benzene ring at 997 $cm^{-1}$ (P1, P2 and P4) and 1002 $cm^{-1}$ (P3 and P5) gradually blue shifted and fused into one single peak with the increase of high pressure. Accordingly, it's reasonable to think that the intermolecular interactions would be enhanced under increasing hydrostatic pressure and this isotropic force mainly influences the intermolecular interactions, where all the molecules are squeezed into a quite uncomfortable condition during the compression process. Once the pressure was released, it can return to the initial state.

Figure 17:
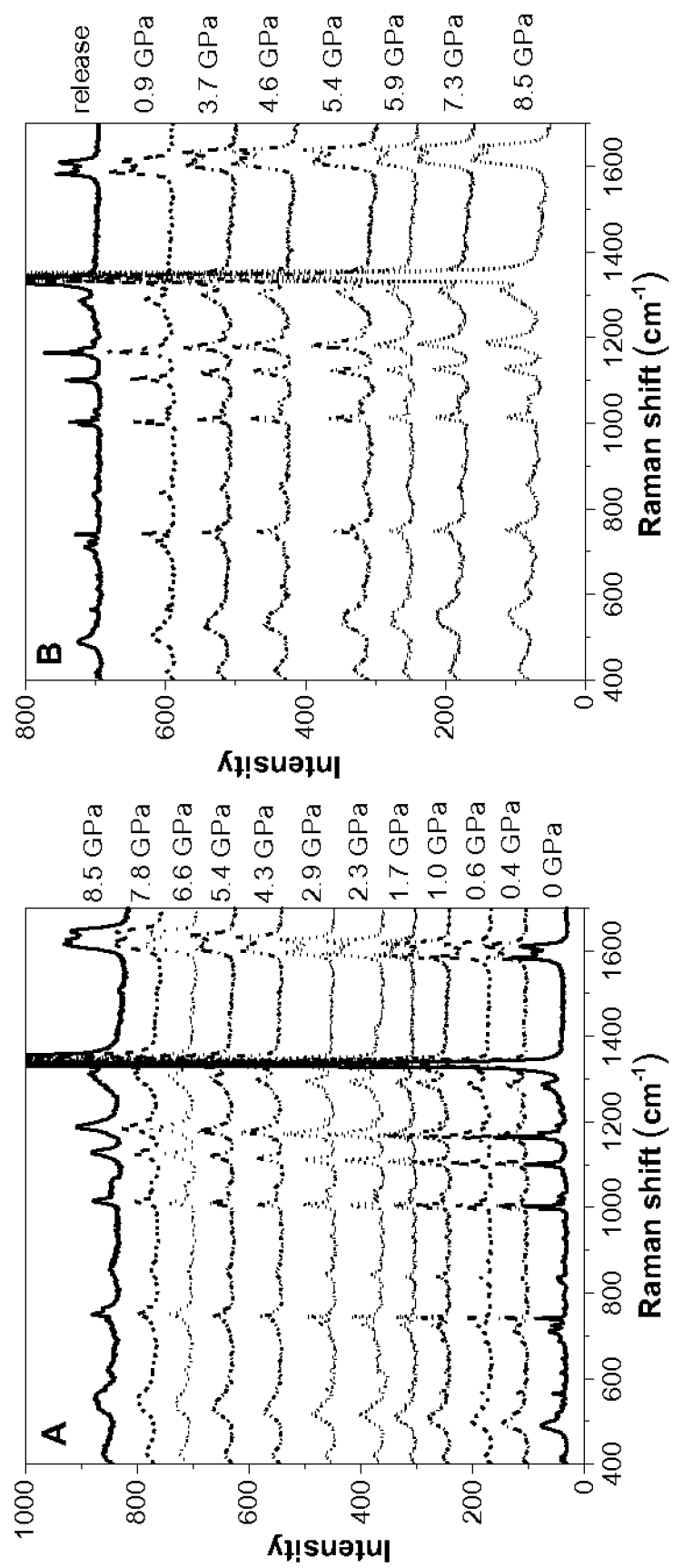
FIG. 17 depicts Raman spectra of AIEgen 1 powder under different pressure values (A: compression; B: decompression). Excitation wavelength was 365 nm
Figure 19:
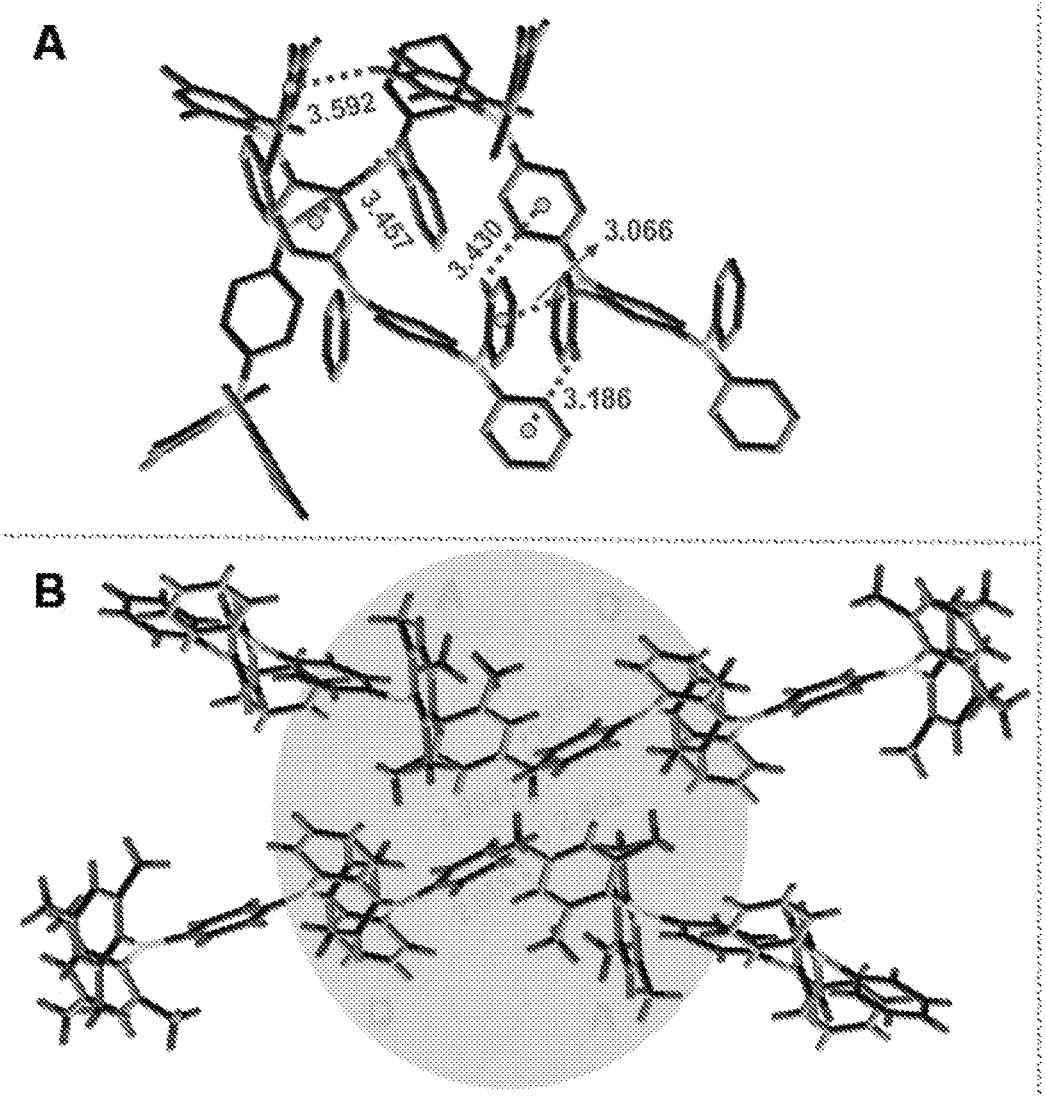
FIG. 19 depicts (A) intermolecular interactions of AIEgen 1 (H atoms except those involved in interactions are omitted for clarity, distance unit: Å). (B) Possible intermolecular charge transfer interactions of AIEgen 1 (D: donor, A: acceptor). (C) Molecular packings of AIEgen 1. Carbon, nitrogen, boron and hydrogen atoms are shown as gray, blue, pink and green.
Figure 19:
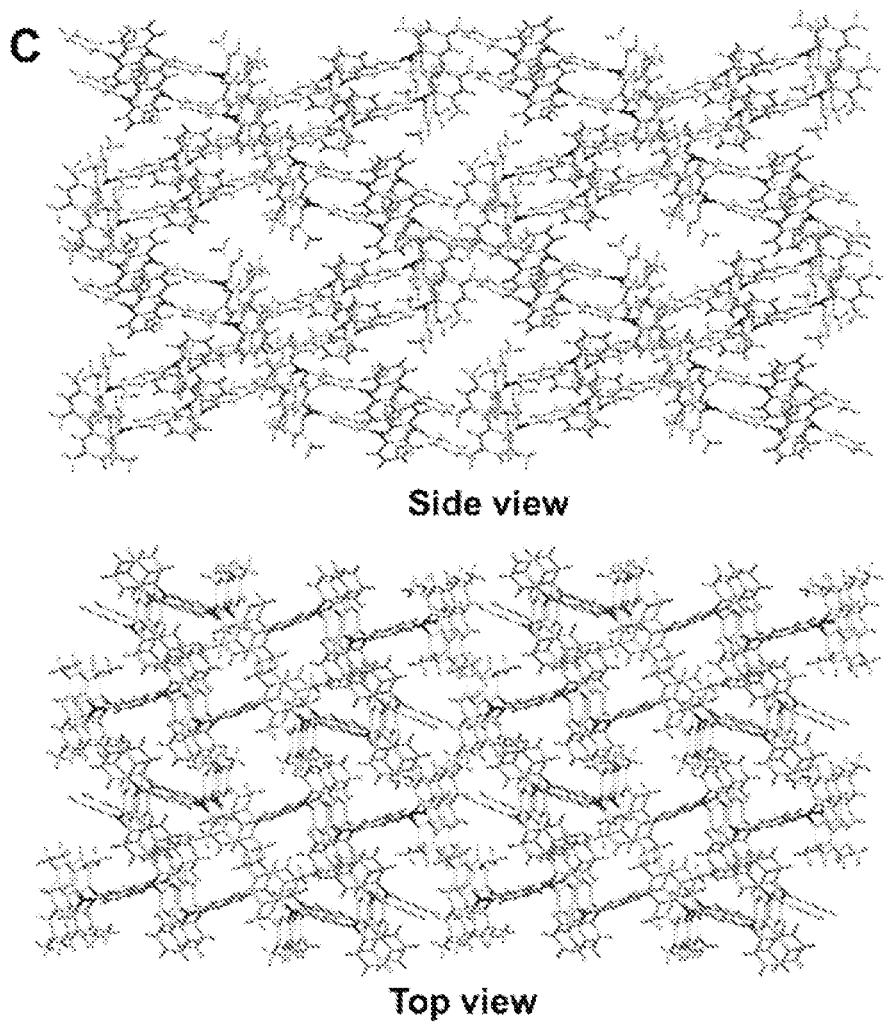

The above observations raise a question: why the mechanical grinding and hydrostatic pressure trigger distinct luminescence alterations? The analyses of crystal structure were expected to provide some clues to address this issue. As shown in FIGS. 17 and 18, multiple weak intermolecular C—H . . . π interactions (distances ranging from 3.06 to 3.43 Å) between the adjacent molecules could be observed, which play a vital role in fixing the orientation of the diamine donor and the triarylboron acceptor (FIG. 17A). Additionally, it was noted that the intermolecular amine donor and the boron acceptor units get very close to each other (FIG. 17B), which is enough to cause intermolecular charge transfer processes. In the molecular packing, the molecules form ordered but very loose arrangements (FIG. 17C). Accordingly, regarding the mechanism of tribochromic PL behavior, it was presumed that these weak intermolecular interactions and the intermolecular charge transfer processes should be perturbed by the anisotropic stimulus of mechanical grinding, which is also accompanied by the intramolecular conformational planarization, and both factors synergistically result in a red-shifted and remarkably enhanced emission. While the situation is presumably different for the piezochromic PL process. The isotropic high pressure is strong enough to squeeze the adjacent molecules close enough that inevitably generates intermolecular π-π interactions and can facilitate intermolecular charge transfer processes, thus jointly leading to the red-shifted and annihilated emission.

Figure 22:
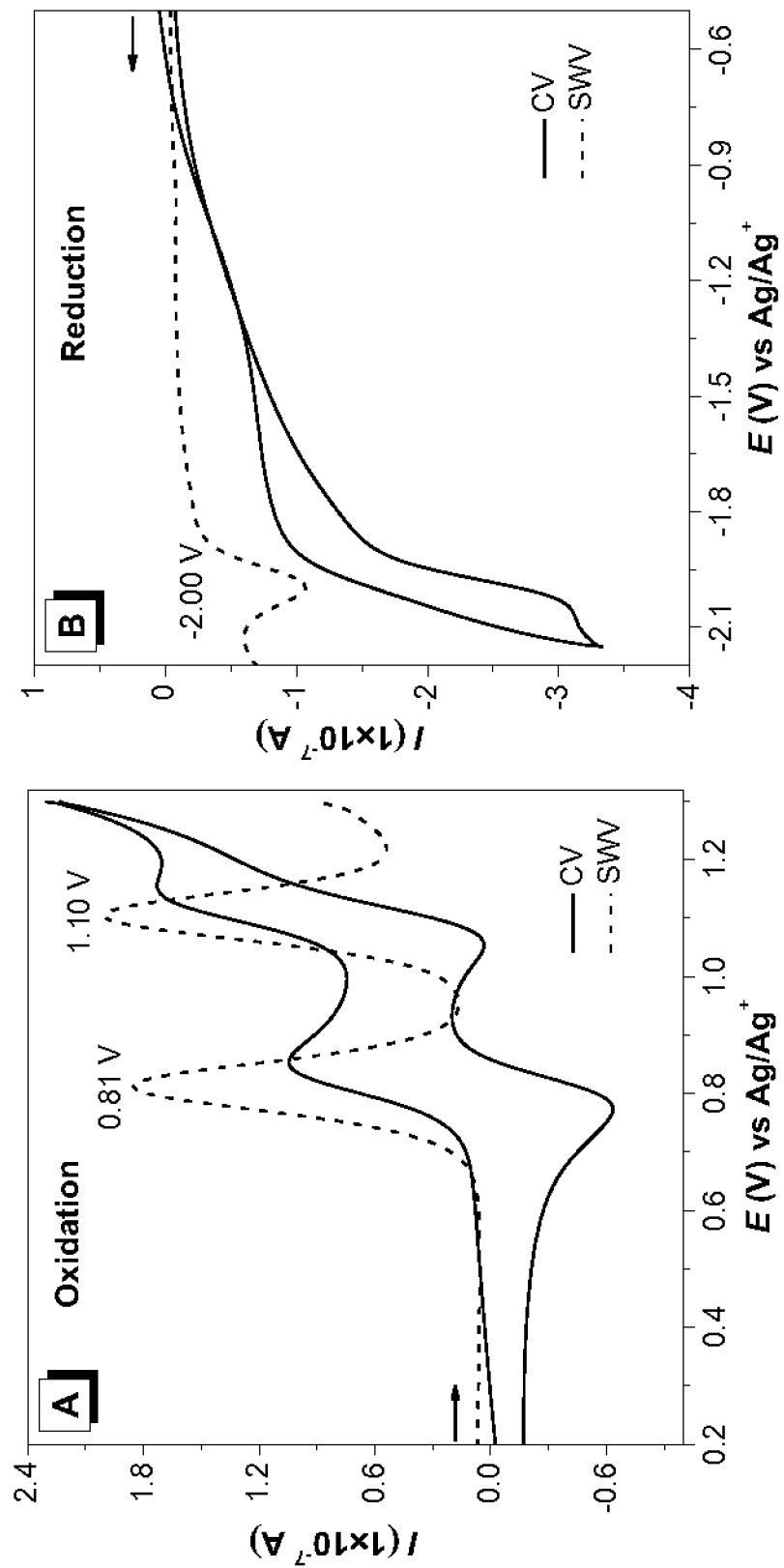
FIG. 22 depicts (A) cyclic voltammogram (black line, THF/0.1 M n-Bu$_4$NPF$_6$, 298 K at 0.1 V s$^1$) and (B) square-wave voltammogram curves (red line, f=10 Hz) of AIEgen 1.

The electrochemical behavior of AIEgen 1 was investigated by cyclic voltammetry and square-wave voltammetry in deaerated $CH_2Cl_2$ containing $10^{-1}$ mol/L $n-Bu_4NPF_6$ as the supporting electrolyte (FIG. 22). AIEgen 1 exhibited two well-defined reversible oxidation peaks at 0.81 and 1.10 V (vs. $Ag/Ag^+$), respectively, and one quasi-reversible reduction peak at -2.00 V (vs. $Ag/Ag^+$). The oxidation peaks are ascribed to stepwise oxidation of the diamine donors and the reduction process is attributed to reduction of the diarylboron acceptor. In addition, the HOMO and LUMO energy levels of AIEgen 1 were determined to be -5.18 and -2.34 eV, respectively, and the HOMO-LUMO band gap was 2.84 eV (Table 4, FIG. 24).

Figure 23:
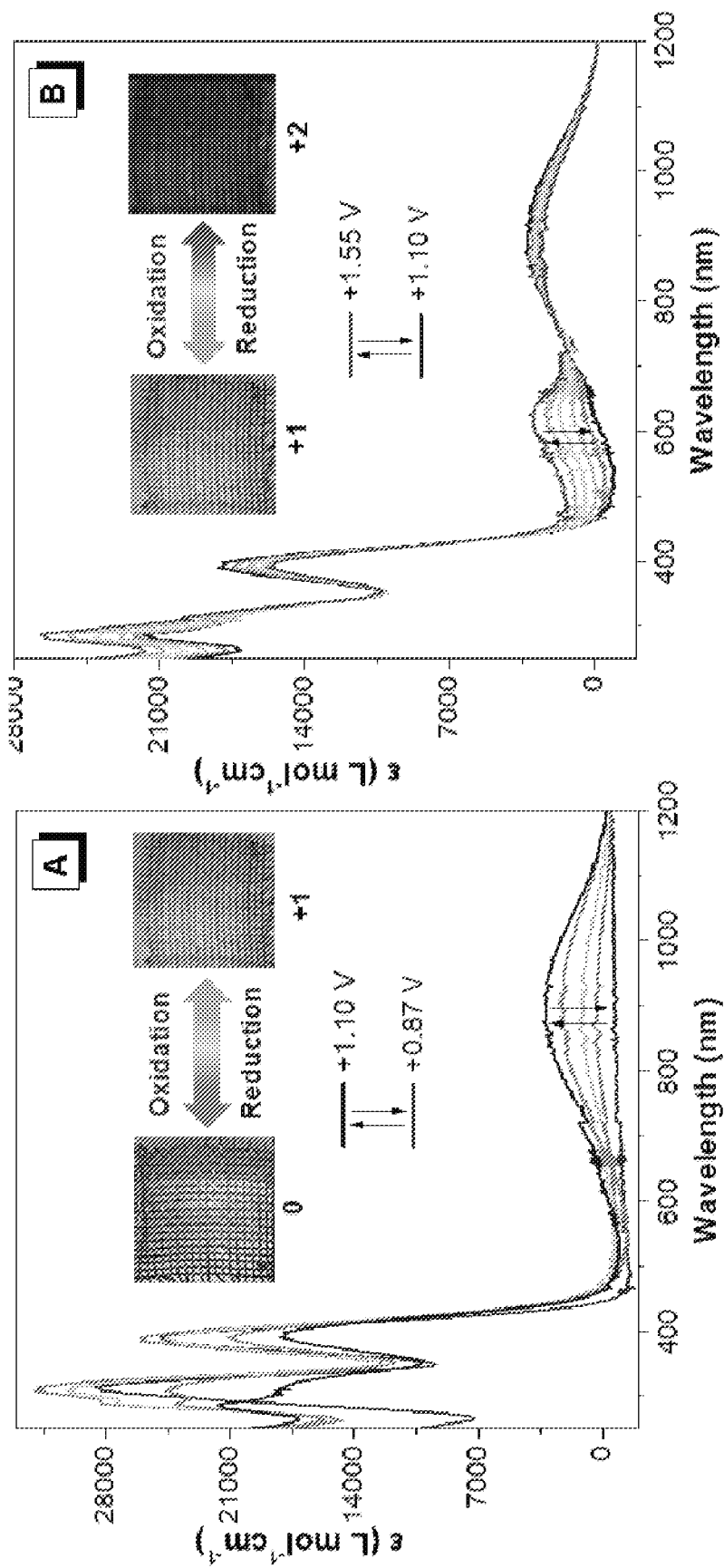
FIG. 23 depicts (A and B) electrochromism and (C) electroluminochromism AIEgen 1 in THF/0.1 M n-Bu$_4$NPF$_6$. Inset: Photos of AIEgen 1 at different oxidation states taken under (A and B) day light and (C) 365 nm UV light.

Interestingly, AIEgen 1 can also respond to the external electric stimulus and exhibited remarkable change in its electronic spectra in the near-infrared (NIR) region and different colors associated with its different oxidation states during the in situ spectroelectrochemical measurements (FIG. 23). As demonstrated in FIG. 23, the completely reversible conversion among three different colors could be readily achieved by modulating the redox potentials of AIEgen 1, i.e. light yellow, vivid green, and dark green, corresponding to neutral, monocationic, and dicationic states, respectively, which could be directly observed with naked eyes. Therefore, the above distinct properties of AIEgen 1 indicate that this compound has great potential to be used as an electroswitchable electrochromic material. Regarding its emission spectra, it can also realize a transformation from turn-on state to turn-off state upon slow oxidation to the mono-cationic state with its orange luminescence gradually weakened (FIG. 23C), also pointing to its potential application in information recording and storage devices.

Figures 23, 24:
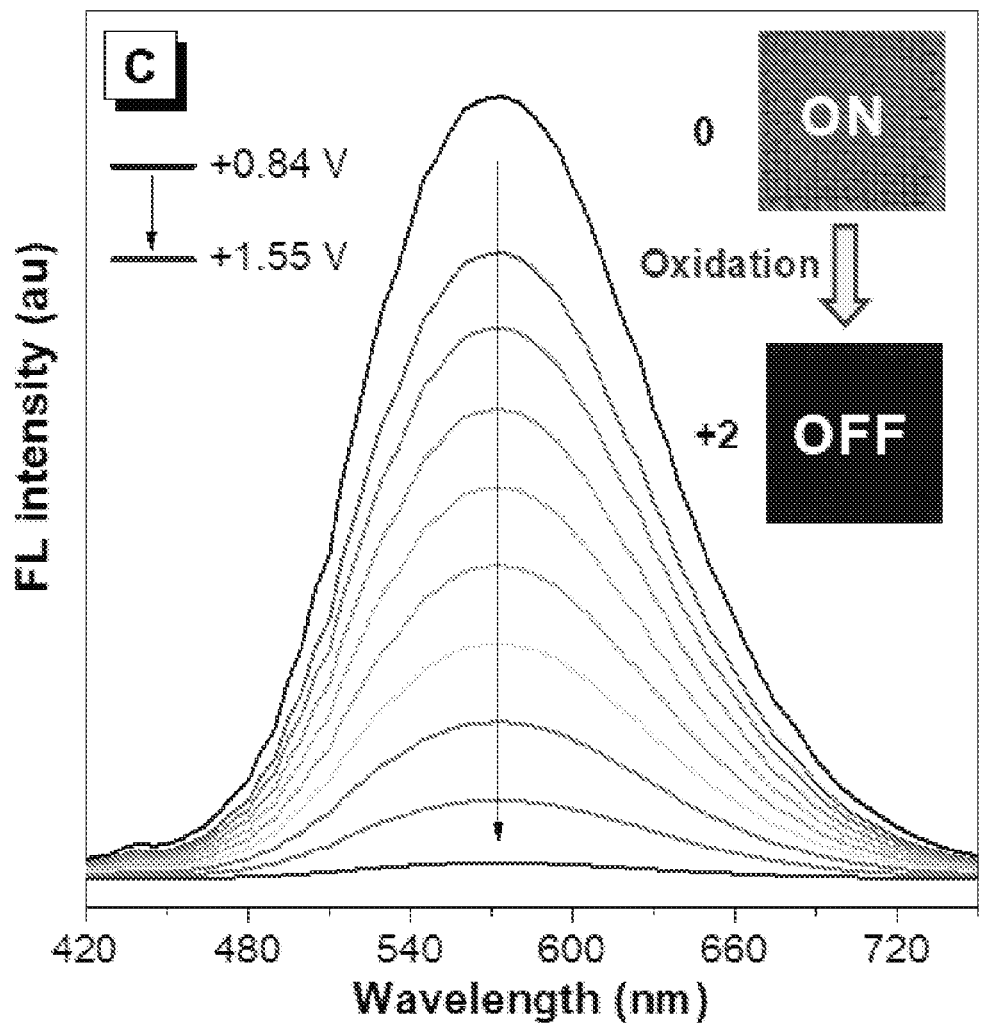
FIG. 24 depicts Table 4 showing photophysical properties of AIEgen 1 at solid state. $^{a)}$ The LUMO energy level was calculated from the HOMO energy level according to the equation HOMO=LUMO–E$_g$ (HOMO=–(4.8+E$_{ox}^{onset}$) eV) and E$_g$ was calculated from the low-energy absorption onset in the absorption spectra according to the equation E$_g$=1240/λ$_{onset}$. $^{b)}$ Solid state. $^{c)}$ Vacuum-deposited on a quartz substrate.
Figure 25:
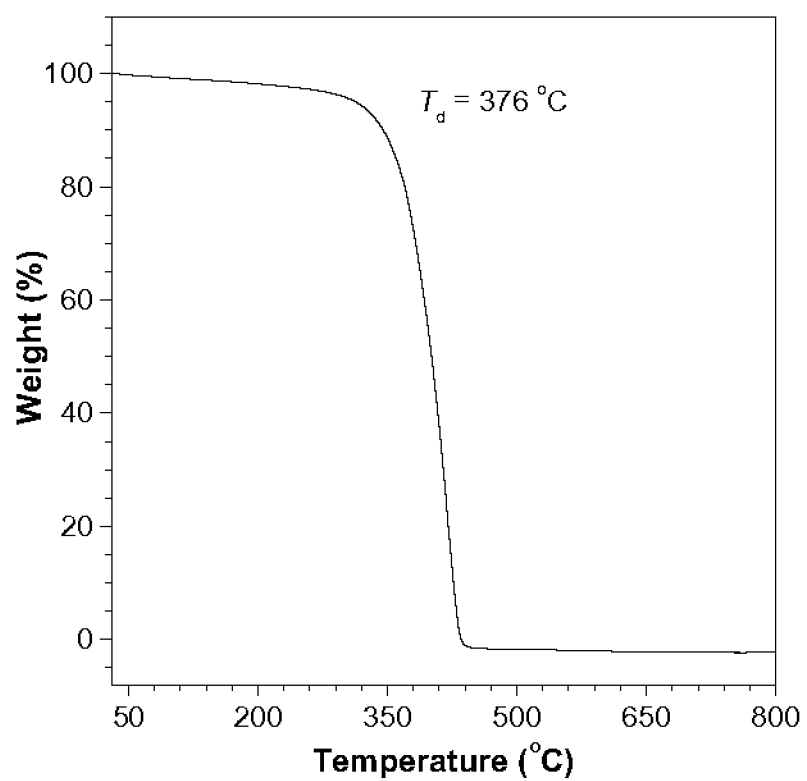
FIG. 25 depicts the thermogravimetric analysis (TGA) curve of AIEgen 1.
Figure 26:
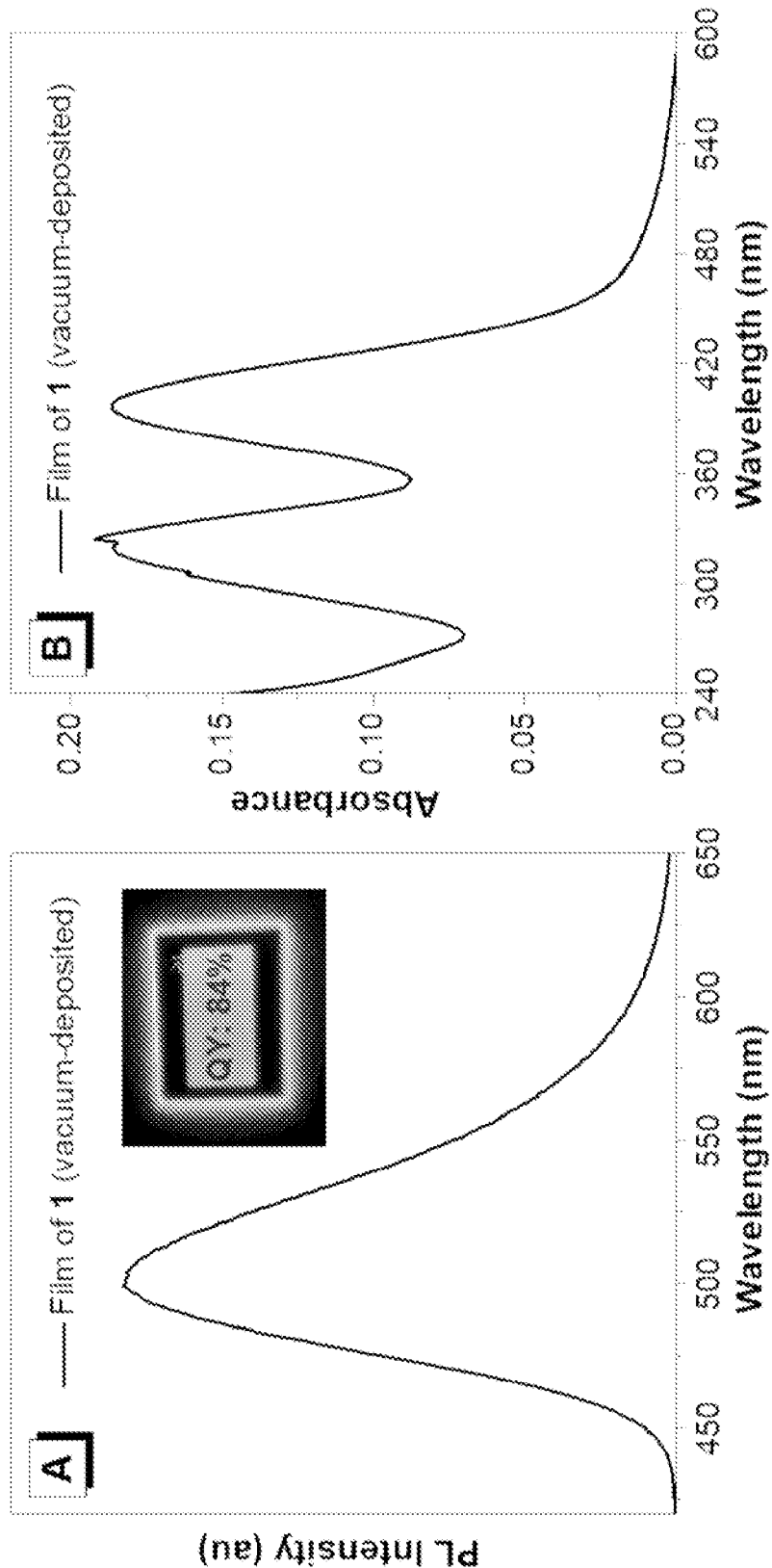
FIG. 26 depicts the (A) PL spectra (Inset: photo taken under 365 nm UV light and its corresponding quantum yield value) and (B) UV spectra as well as lifetime (C) of the film for AIEgen 1 obtained by vacuum evaporation.
Figure 26:
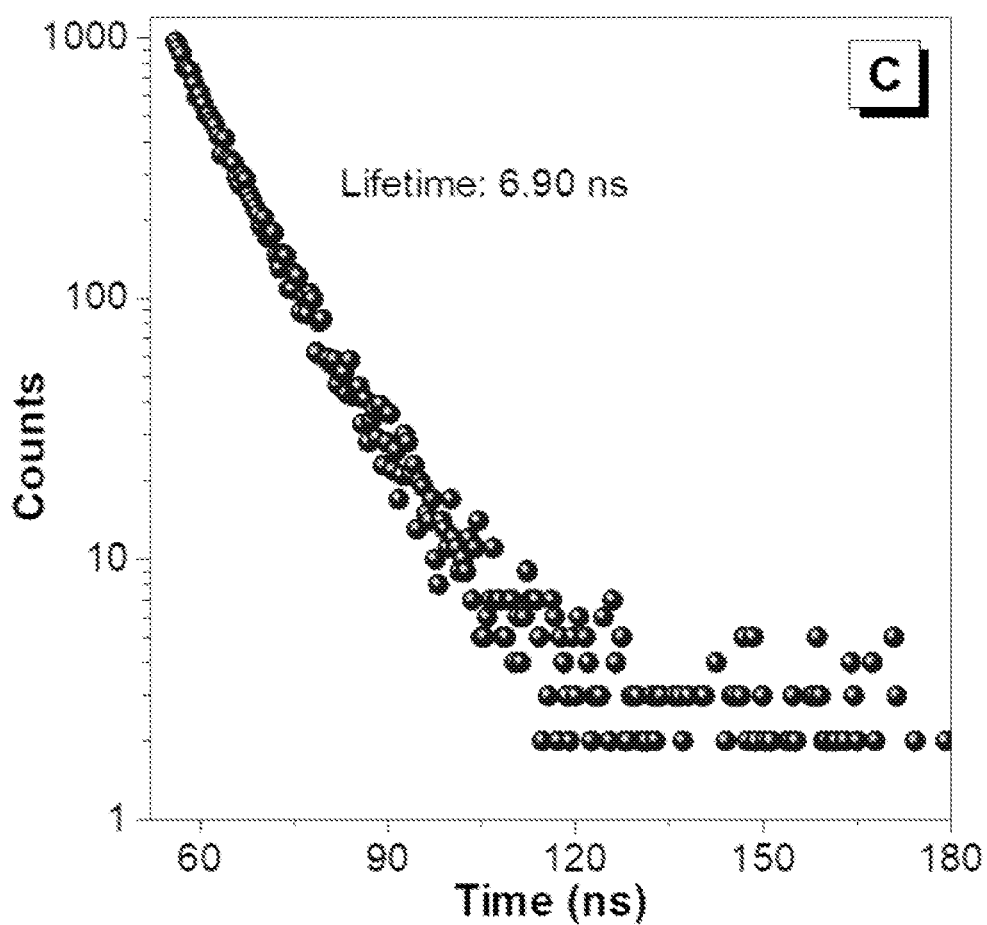
Figure 27:
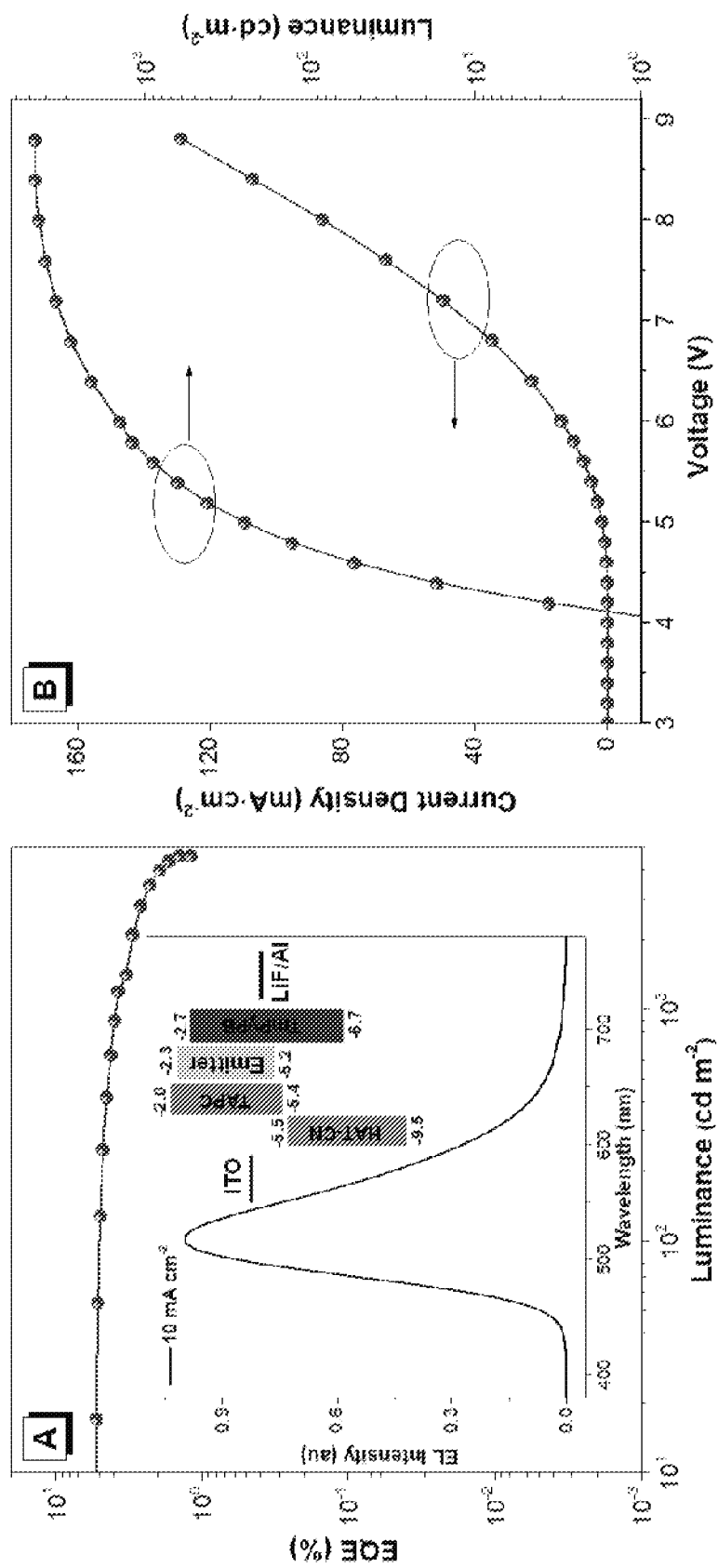
FIG. 27 depicts the (A) EQE versus brightness curve (inset: EL spectrum at 10 mA cm$^{-2}$), (B) Current density-voltage-luminance plot, (C) Voltage-dependent EL spectra and (D) CE and PE versus brightness curve of a EL device with a configuration of indium tin oxide (ITO)/1,4,5,8,9,11-hexaazatriphenylenehexacarbonitrile (HATCN) (5 nm)/1,1-bis[(di-4-tolylamino)phenyl]cyclohexane (TAPC) (25 nm)/AIEgen 1 (35 nm)/1,3,5-tri(m-pyridin-3-ylphenyl)benzene, 1,3,5-Tris(3-pyridyl-3-phenyl)benzene TmPyPB (55 nm)/LiF (1 nm)/Al.
Figure 27:
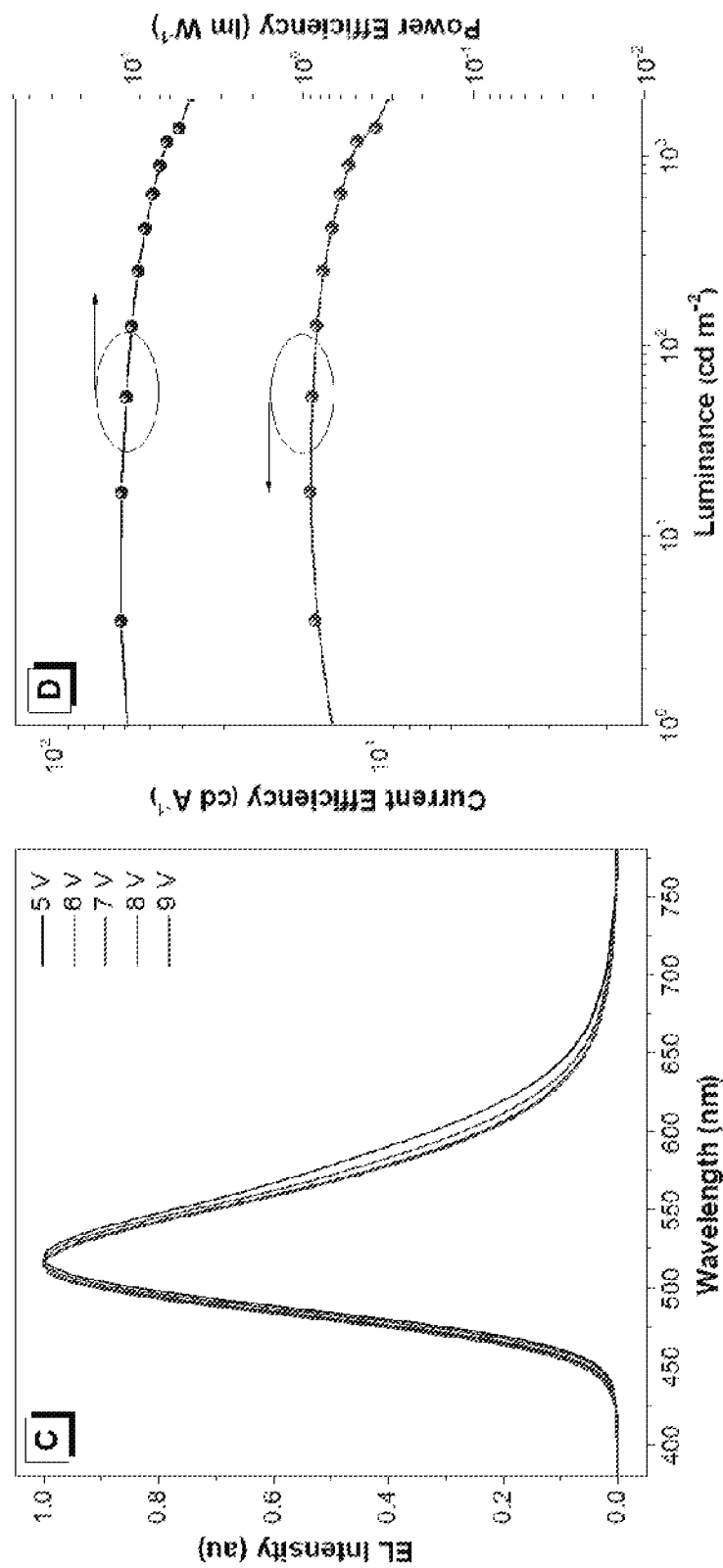

In light of its excellent luminescent behavior of AIEgen 1 in the solid state, its potential application as solid-state emitter was evaluated. Thermogravimetric analysis (TGA) was also performed to analyze the thermal properties of AIEgen 1 under nitrogen atmosphere, as shown in FIG. 25 and Table 4 (FIG. 24). The pertinent data indicated that AIEgen 1 exhibits desirable thermal stability with a decomposition temperature up to 376° C., thus demonstrating that this compound is stable enough for thermal evaporation. Its film was prepared by vacuum evaporation. As shown in FIG. 26, its film exhibited a very bright yellow-green fluorescence (τ=6.9 ns) with a maximal peak at 501 nm and a very high quantum yield of 84%, thus indicating very similar properties to its ground amorphous state we discussed above. Accordingly, we further fabricated non-doped OLED with the device configuration of indium tin oxide ITO/ HATCN (5 nm)/TAPC (25 nm)/AIEgen 1 (35 nm)/TmPyPB (55 nm)/LiF (1 nm)/Al (120 nm), wherein HATCN and LiF serve as the hole-injection and electron-injection layers, respectively; TAPC and TmPyPB serve as the hole-transport and electron-transport layers, respectively; AIEgen 1 serves as the light-emitting layer; and ITO (indium tin oxide) and Al are used as the anode and electrode, respectively. The schematic energy level diagrams of the devices, EQE (external quantum efficiency) versus luminance curves, the electroluminescence (EL) spectra, the current density-voltage-luminance (J-V-L) characteristics, voltage-dependent EL spectra, the current efficiency and power versus luminance curves of the non-doped OLEDs are presented in FIG. 27. The key device performances are summarized in Table 5 (FIG. 28). The EL spectra of AIEgen 1 is close to that of the nondoped PL spectrum (vacuum-deposited) and very stable at various driving voltages, indicating that the emissive excitons were well confined in the emitting layer. The EL shows a bright green emission peak of 516 nm and CIE coordinate of (0.289, 0.551). The maximum luminance ($L_{max}$), current efficiency ($\eta_c$), power efficiency ($\eta_p$), and EQE values are as high as 4622 cd m$^{-2}$, 16.23 cd A$^{-1}$, 11.69 lm W$^{-1}$, and 5.22%, respectively. Impressively, the EQE value (5.22%) is practically reaching the theoretical limit value of traditional organic emitters, which makes the compounds described herein, and parituclarly AIEgen 1, a promising candidate for OLED application.

EXAMPLES

The following examples are illustrative of the presently described subject matter and are not intended to be limitations thereon.

Preparation of AIEgen 1

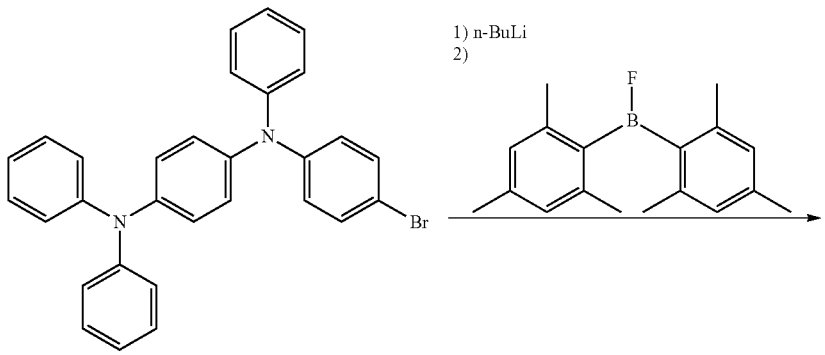

Precursor 1

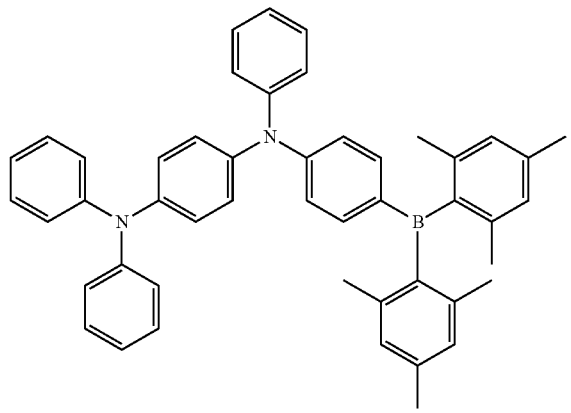

AIEgen 1

The general synthetic route to AIEgen 1 is outlined above. All manipulations were carried out under a dry argon atmosphere using standard Schlenk techniques, unless stated otherwise. Solvents were pre-dried and distilled under argon prior to use, except those used directly for spectroscopic measurements, which were of spectroscopic grade. The precursor 1 was prepared according to procedure described in the literature (*J. Phys. Chem. A,* 2015,119, 1933-1942.). Other reagents were purchased and used as received.

Synthesis of AIEgen 1: $N^1$-(4-bromophenyl)-N,$N^4$,$N^4$-triphenylbenzene-1,4-diamine (Precursor 1) (490 mg, 1.00 mmol) was dissolved in anhydrous THF (30 mL) under nitrogen, and the resulting mixture was cooled to −78° C. To this solution, n-BuLi (0.5 mL, 2.5 M in hexane) was added slowly and the resulting solution was stirred for 1 h at −78° C. Dimesitylboron fluoride (402 mg, 1.5 mmol) was dissolved in THF (10 mL) and then slowly added to the reaction solution at −78° C. The mixture was allowed to warm to room temperature with stirring overnight. The solvent was then removed in vacuo, and the residue was purified by chromatography on silica gel (petroleum ether/dichloromethane 8:1, v/v). The product was precipitated from a solution in $CH_2Cl_2$ by adding MeOH to give 547 mg (79%) of AIEgen 1 as a yellow-green powder. $^1$H NMR ($CDC_3$, 400 MHz, ppm): δ 7.35 (d, J=8 Hz, 2H), 7.18-7.31 (m, 8H), 6.98-7.10 (m, 11H), 6.90 (d, J=8 Hz, 2H), 6.79 (s, 4H), 2.28 (s, 6H), 2.06 (s, 12H); $^{13}$C NMR ($CDC_3$, 100 MHz, ppm): 151.4, 147.7, 146.6, 144.2, 141.9, 141.2, 140.7, 138.7, 137.9, 129.4, 129.2, 129.1, 128.0, 127.1, 125.6, 124.9, 124.1, 124.0, 122.7, 118.9 (Ar); HRMS (MALDI-TOF): m/z: [M]+ calcd for $C_{48}H_{45}BN_2^+$: 660.3676; found: 660.3665.

What is claimed is:

1. A compound having Formula 8:

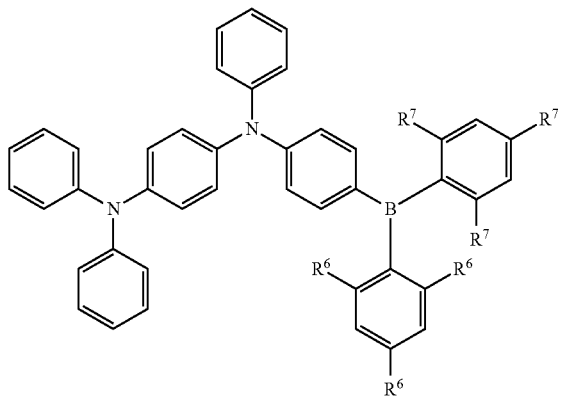

8 wherein each of $R^6$ and $R^7$ is independently selected from hydrogen and alkyl.

2. The compound of claim 1, wherein each of $R^6$ and $R^7$ is methyl.

3. A method of preparing the compound of claim 1, the method comprising: contacting a compound of Formula:

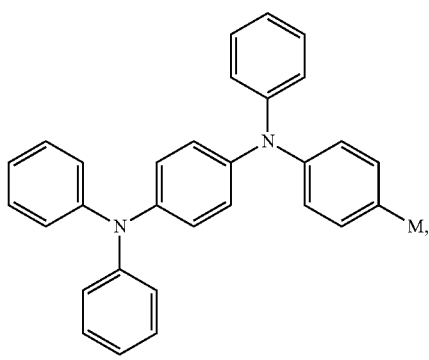

wherein M is lithium, sodium, MgBr, or a Zn species with a compound of Formula:

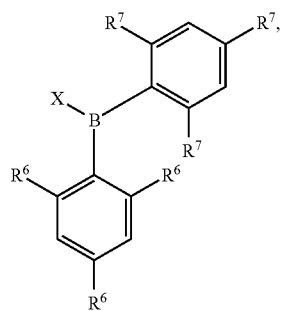

wherein each of $R^6$ and $R^7$ is independently selected from hydrogen and alkyl; and X is a halide; thereby forming the compound of claim 1.

4. A method for detecting a change in a physical-chemical parameter in a test sample comprising the compound of claim 1, the method comprising: providing the test sample; measuring a fluorescence emission of the test sample; comparing a measured fluorescence emission of the test sample with a fluorescence emission of a control sample comprising the compound of claim 1 in a ground state; and based on the difference in fluorescence emission between the test sample and the control sample determine whether there is a change in the physical-chemical parameter, wherein the ground state is a fluorescence emission of the compound of claim 1 in the absence of the physical-chemical parameter.

5. The method of claim 4, Wherein the physical-chemical parameter is at least one parameter selected from the group consisting of a temperature of the test sample, a sheer force exerted on the test sample, an oxidation state of the test sample, a solvent in the test sample; and an isotropic hydrostatic pressure of the test sample.

6. The method claim 4, wherein the compound has the formula;

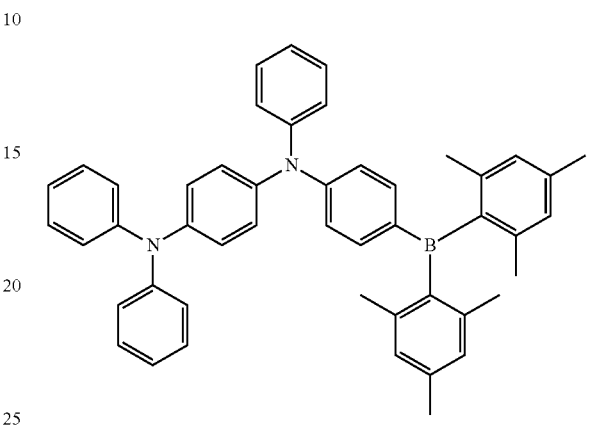

7. An organic light emitting diode (OLED) comprising the compound of claim 1.

8. The organic light emittig diodo (OLED) of claim 7, wherein the compound has the formula:

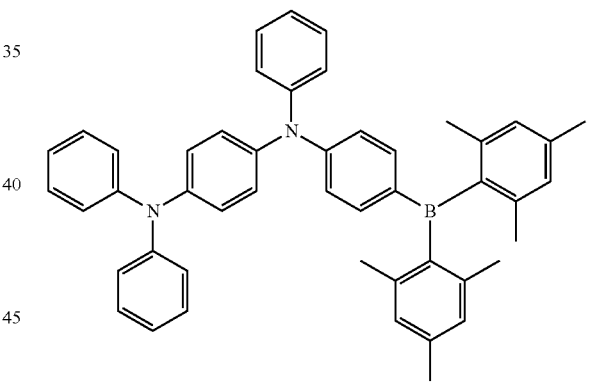

* * * * *